(12) United States Patent  
Sasaki et al.

(10) Patent No.: US 12,138,098 B2
(45) Date of Patent: Nov. 12, 2024

(54) MEDICAL IMAGE PROCESSING APPARATUS, X-RAY DIAGNOSTIC APPARATUS, AND MEDICAL IMAGE PROCESSING METHOD

(71) Applicant: CANON MEDICAL SYSTEMS CORPORATION, Otawara (JP)

(72) Inventors: Sho Sasaki, Utsunomiya (JP); Yusaku Aizawa, Utsunomiya (JP); Kodai Hirayama, Nasushiobara (JP); Ryoichi Nagae, Nasushiobara (JP); Tomoki Fujito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 399 days.

(21) Appl. No.: 17/390,300

(22) Filed: Jul. 30, 2021

(65) Prior Publication Data

US 2022/0031277 A1 Feb. 3, 2022

(30) Foreign Application Priority Data

Jul. 30, 2020 (JP) .................................. 2020-129283
Aug. 3, 2020 (JP) .................................. 2020-131435
Jul. 29, 2021 (JP) .................................. 2021-124826

(51) Int. Cl.
*G06K 9/00* (2022.01)
*A61B 6/00* (2024.01)
(Continued)

(52) U.S. Cl.
CPC .............. *A61B 6/5264* (2013.01); *A61B 6/12* (2013.01); *A61B 6/504* (2013.01); *G06F 18/22* (2023.01);
(Continued)

(58) Field of Classification Search
CPC .. G06K 9/00; A61B 6/469; A61B 6/00; A61K 35/12
(Continued)

(56) References Cited

U.S. PATENT DOCUMENTS 11,058,386 B2 * 7/2021 Shima .................... A61B 6/504
2012/0163534 A1 * 6/2012 Nambu .................. A61B 6/486
378/44

(Continued)

FOREIGN PATENT DOCUMENTS

JP 58-216038 A 12/1983
JP 2011-156321 A 8/2011
(Continued)

OTHER PUBLICATIONS

Indian Office Action issued May 20, 2022 in Indian Patent Application No. 202144034366, citing references AA and AB therein, 8 pages.
(Continued)

*Primary Examiner* — Seyed H Azarian
(74) *Attorney, Agent, or Firm* — Oblon, McClelland, Maier & Neustadt, L.L.P.

(57) ABSTRACT

A medical information processing device according to an embodiment includes processing circuitry configured to acquire a plurality of X-ray images including a device inserted into a body of a subject, suppress movement of a characteristic portion characterized in a shape that is positioned distant from a distal end of the device among the X-ray images, and output the X-ray images in which movement of the characteristic portion is suppressed.

22 Claims, 16 Drawing Sheets

(51) Int. Cl.
  *A61B 6/12* (2006.01)
  *A61B 6/50* (2024.01)
  *G06F 18/22* (2023.01)
  *G06T 7/00* (2017.01)
  *G06T 7/20* (2017.01)

(52) U.S. Cl.
  CPC .............. *G06T 7/0016* (2013.01); *G06T 7/20* (2013.01); *G06T 2207/10116* (2013.01); *G06T 2207/30048* (2013.01); *G06T 2207/30101* (2013.01); *G06V 2201/034* (2022.01)

(58) Field of Classification Search
  USPC ........ 382/100, 103, 106–107, 128–134, 154, 382/156, 162, 168, 173, 177, 181, 199, 382/203, 219, 224, 254, 274, 285, 291, 382/305, 321; 378/4, 21, 44, 28
  See application file for complete search history.

(56) References Cited

U.S. PATENT DOCUMENTS

| | | | |
|---|---|---|---|
| 2012/0250973 A1* | 10/2012 | Nambu | A61B 6/469 382/132 |
| 2015/0161790 A1 | 6/2015 | Takahashi et al. | |
| 2015/0302584 A1 | 10/2015 | Brauner et al. | |
| 2016/0331470 A1* | 11/2016 | Sato | A61M 5/158 |
| 2018/0174297 A1 | 6/2018 | Ooga et al. | |
| 2019/0087955 A1* | 3/2019 | Takahashi | G06T 7/0012 |
| 2019/0159756 A1* | 5/2019 | Coats | A61B 8/445 |
| 2019/0159759 A1* | 5/2019 | Murakami | A61B 8/12 |

FOREIGN PATENT DOCUMENTS

| | | |
|---|---|---|
| JP | 2013-158372 A | 8/2013 |
| JP | 2017-153621 A | 9/2017 |
| JP | 2018-183645 A | 11/2018 |
| JP | 2019-118710 A | 7/2019 |
| WO | WO 2016/046289 A1 | 3/2016 |

OTHER PUBLICATIONS

Oral Hearing issued May 16, 2024, in Indian Patent Application No. 202144034366 (citing reference 15 therein), 3 pages.

Japanese Office Action mailed on Feb. 20, 2024, in Japanese Patent Application No. 2020-131435, citing documents 15-16, therein, 3 total pages.

* cited by examiner

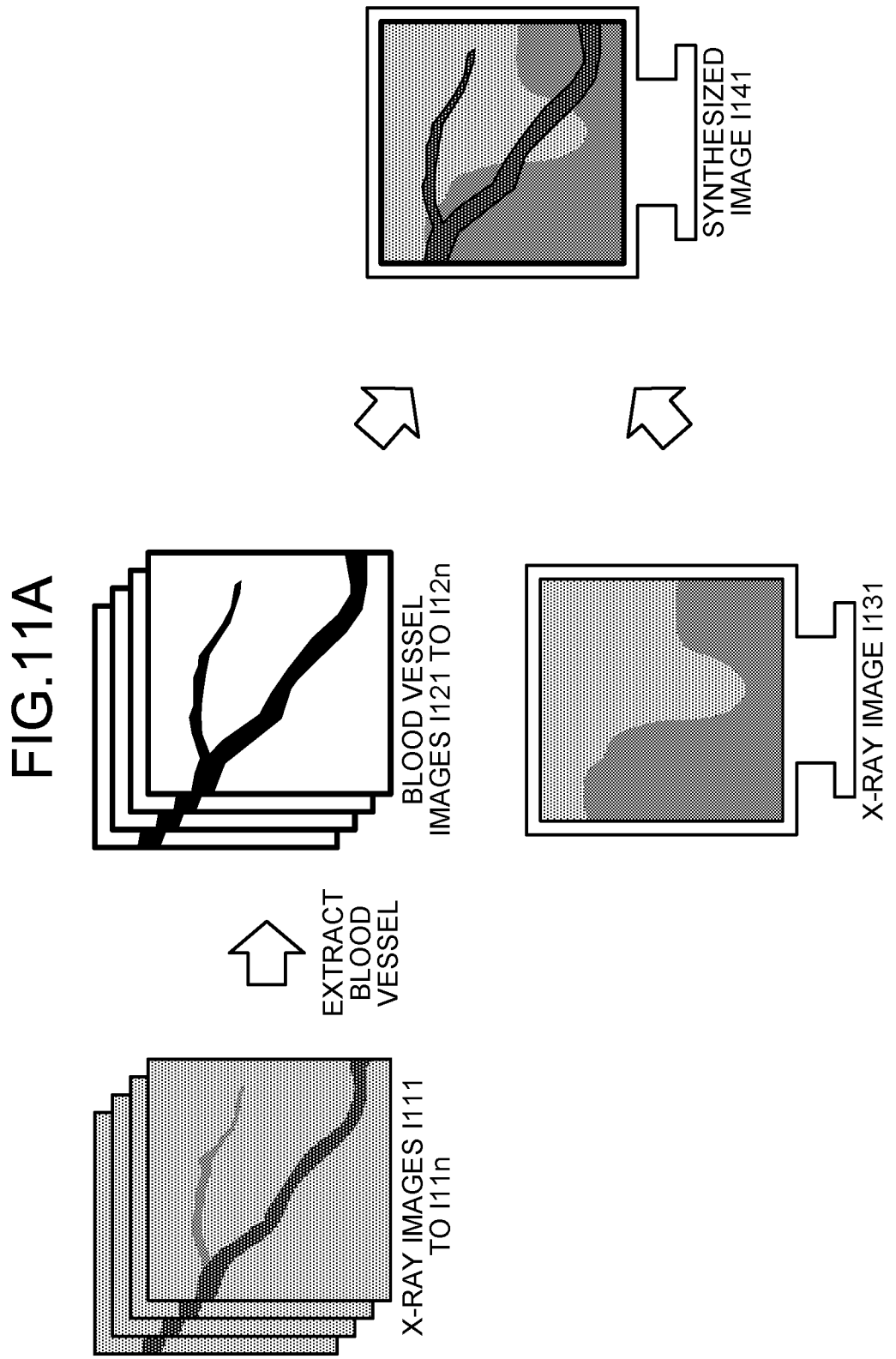

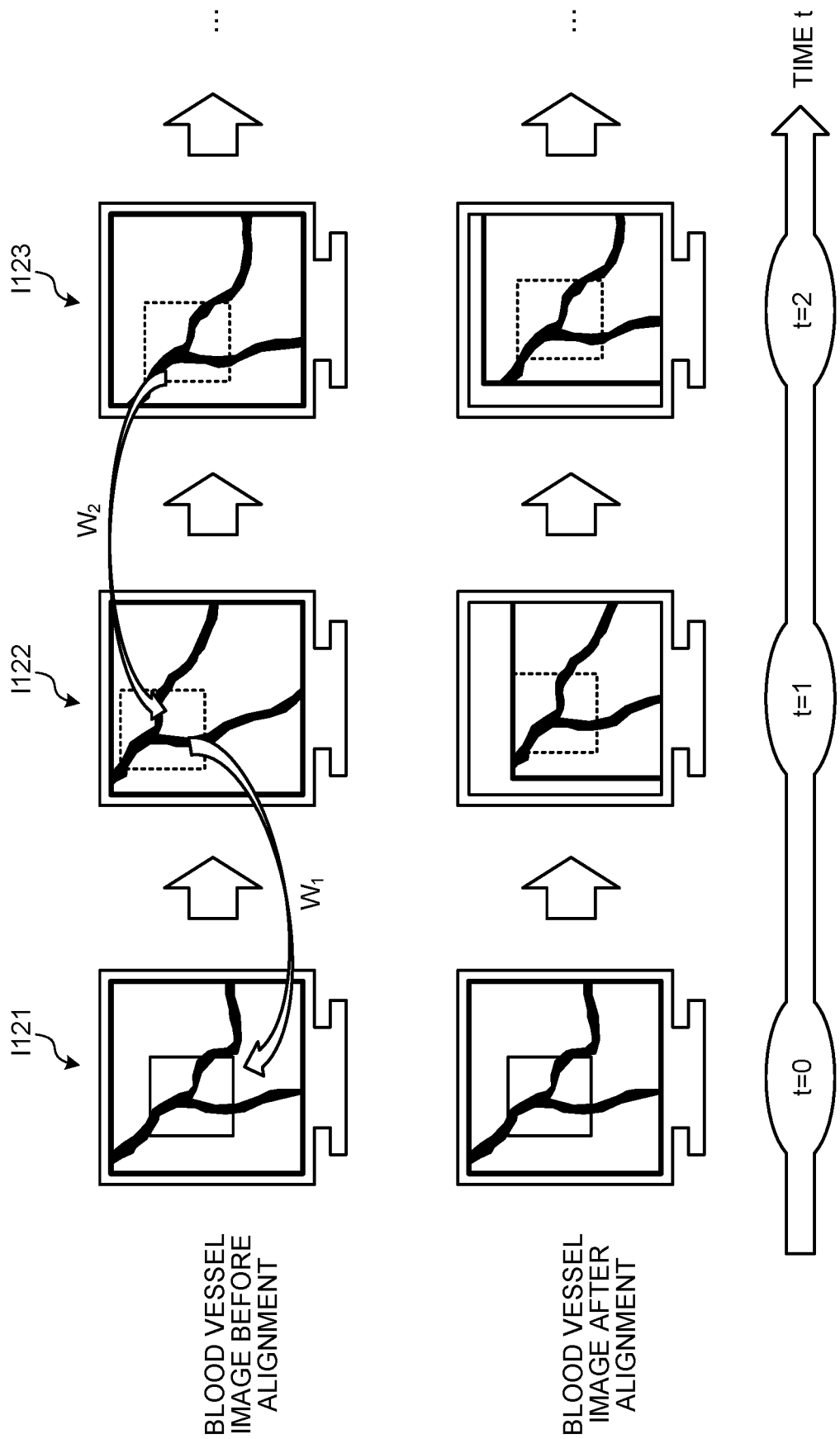

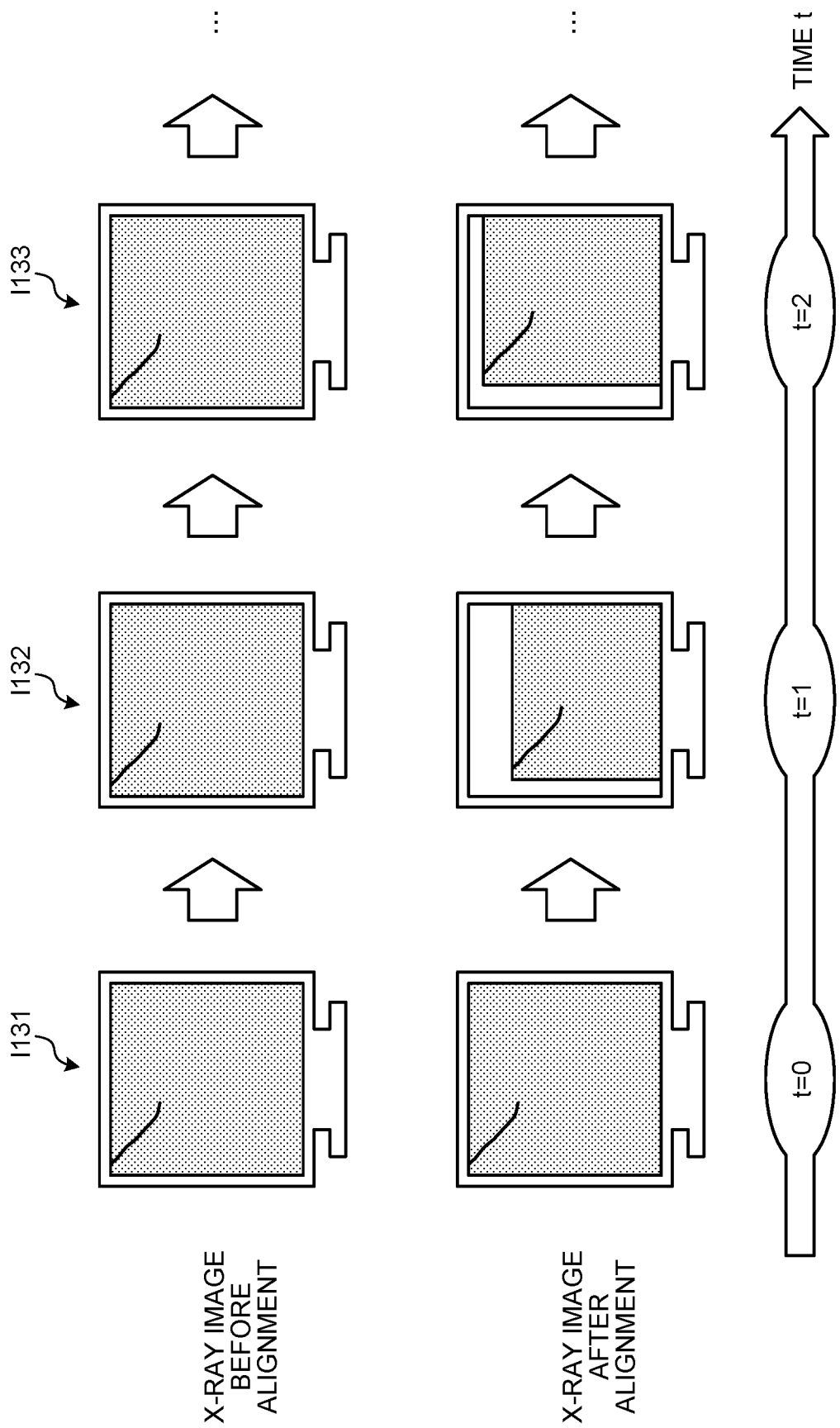

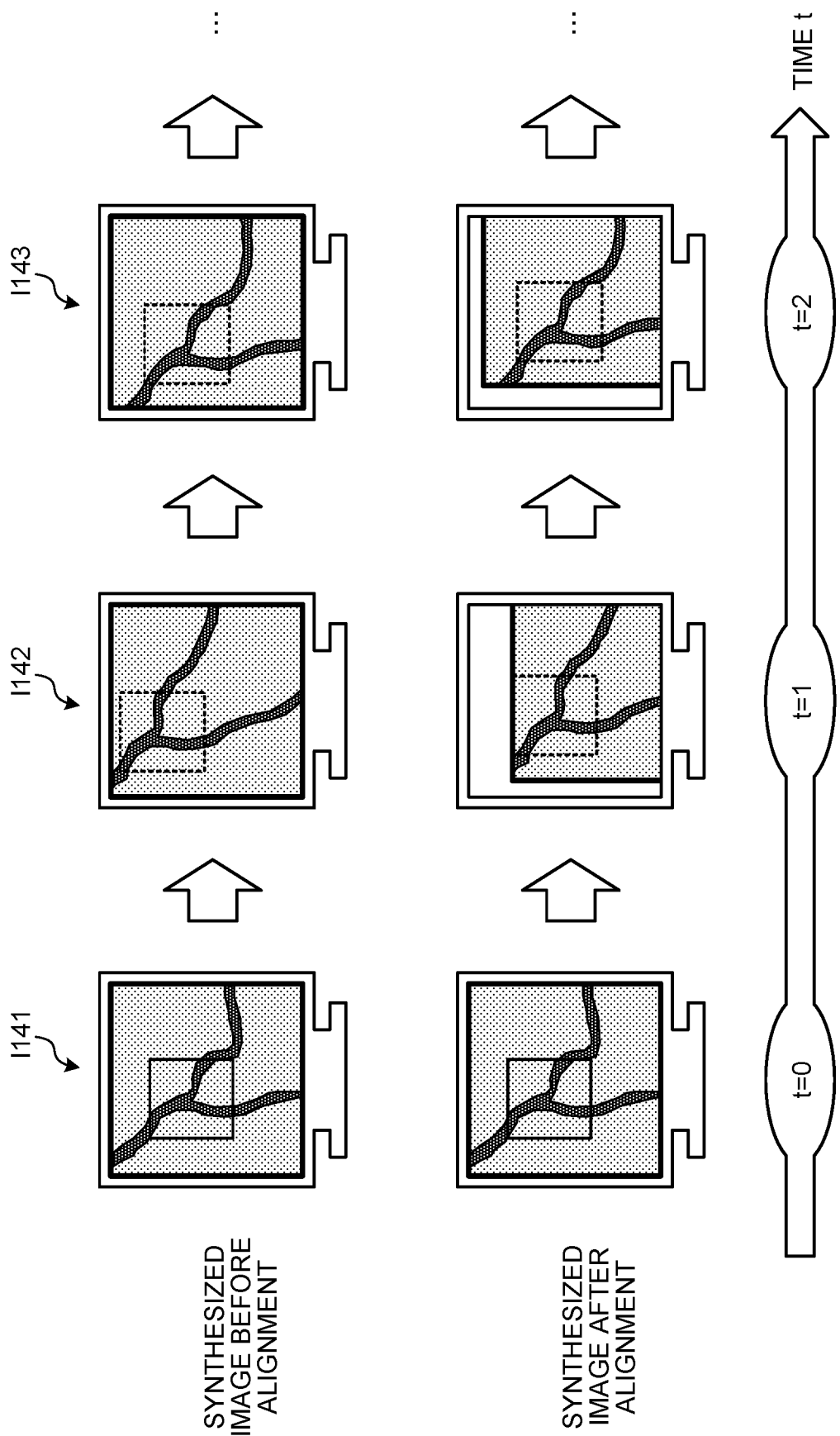

MEDICAL IMAGE PROCESSING APPARATUS, X-RAY DIAGNOSTIC APPARATUS, AND MEDICAL IMAGE PROCESSING METHOD

CROSS-REFERENCE TO RELATED APPLICATIONS

This application is based upon and claims the benefit of priority from Japanese Patent Application No. 2020-129283, filed on Jul. 30, 2020, Japanese Patent Application No. 2020-131435, filed on Aug. 3, 2020, and Japanese Patent Application No. 2021-124826, filed on Jul. 29, 2021; the entire contents of which are incorporated herein by reference.

FIELD

Embodiments described herein relate generally to a medical image processing apparatus, an X-ray diagnostic apparatus, and a medical image processing method.

BACKGROUND

There are known various intravascular treatment techniques performed by inserting a device such as a catheter or a guide wire into a blood vessel of a subject. In performing intravascular treatment, an X-ray image is acquired and displayed for assisting a device operation performed by an operator. In this case, the device may move on the X-ray image depending on a treatment target site, and observation may be difficult to be performed.

Although a blood vessel shape does not typically appear on the X-ray image, a blood vessel image acquired in advance may be displayed in some cases for assisting the device operation in the blood vessel. In this case, the image may move due to influence of heartbeat, respiration, and the like depending on the treatment target site, and observation may be difficult to be performed.

BRIEF DESCRIPTION OF THE DRAWINGS

FIG. 11A is a diagram illustrating a display example according to the third embodiment;

FIG. 12A is a diagram for explaining first processing and second processing according to the third embodiment;

FIG. 12B is a diagram for explaining the first processing and the second processing according to the third embodiment;

FIG. 12C is a diagram for explaining the first processing and the second processing according to the third embodiment;

DETAILED DESCRIPTION

The following describes embodiments of a medical image processing apparatus, an X-ray diagnostic apparatus, and a computer program in detail with reference to the attached drawings.

First Embodiment

Figure 1:
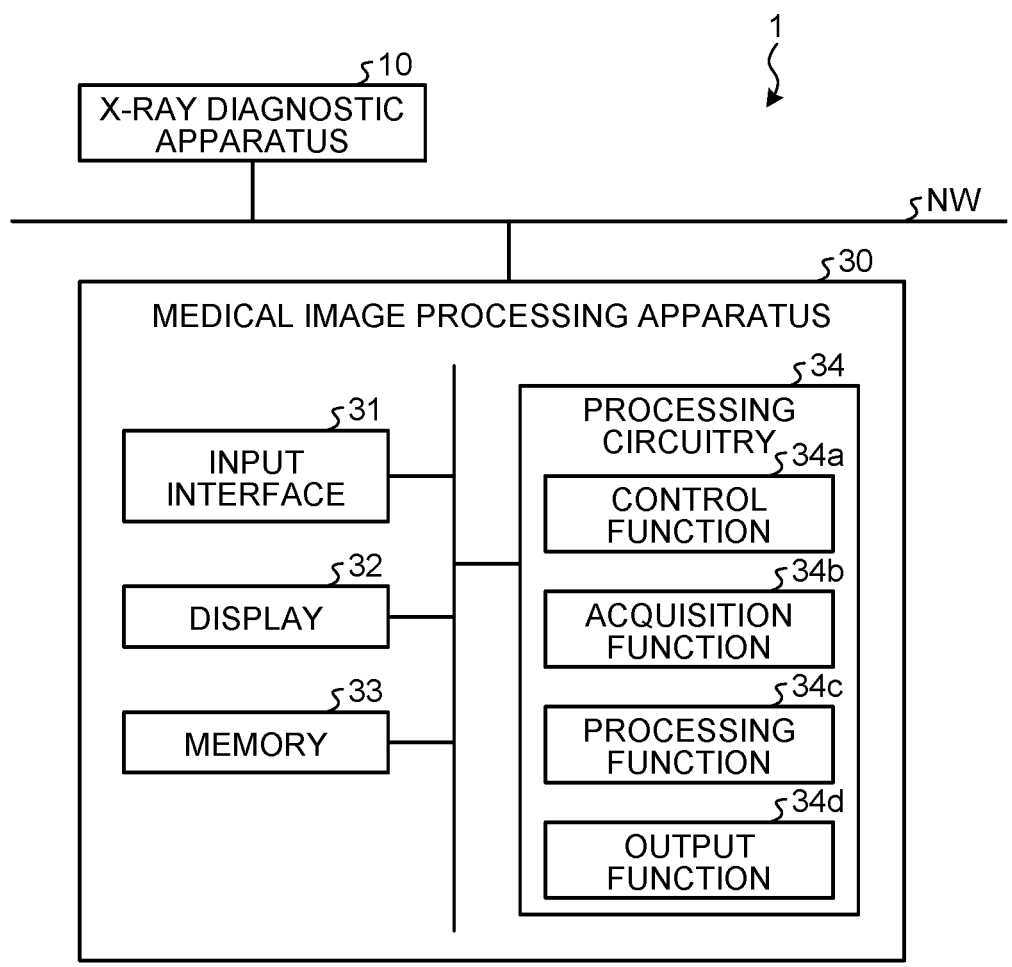
FIG. 1 is a block diagram illustrating an example of a configuration of a medical image processing system according to a first embodiment.

A first embodiment describes a medical image processing system 1 illustrated in FIG. 1 as an example. For example, the medical image processing system 1 includes an X-ray diagnostic apparatus 10 and a medical image processing apparatus 30. The X-ray diagnostic apparatus 10 and the medical image processing apparatus 30 are connected to each other via a network NW. FIG. 1 is a block diagram illustrating an example of a configuration of the medical image processing system 1 according to the first embodiment.

The X-ray diagnostic apparatus 10 is a device for acquiring X-ray images from a subject P1. For example, while intravascular treatment is given to the subject P1, the X-ray diagnostic apparatus 10 acquires two-dimensional X-ray images from the subject P1 over time while intravascular treatment is performed for the subject P, and successively transmits the acquired X-ray images to the medical image processing apparatus 30. A configuration of the X-ray diagnostic apparatus 10 will be described later.

The medical image processing apparatus 30 acquires the X-ray images acquired by the X-ray diagnostic apparatus 10, and performs various kinds of processing using the X-ray images. For example, the medical image processing apparatus 30 performs processing for improving visibility of a device on the X-ray image, and presents the X-ray image after the processing to a user. For example, as illustrated in FIG. 1, the medical image processing apparatus 30 includes an input interface 31, a display 32, a memory 33, and processing circuitry 34.

The input interface 31 receives various input operations from the user, and converts the received input operations into electric signals to be output to the processing circuitry 34. For example, the input interface 31 is implemented by a mouse, a keyboard, a trackball, a switch, a button, a joystick, a touch pad with which an input operation is performed by touching an operation surface thereof, a touch screen obtained by integrating a display screen with a touch pad, a noncontact input circuit using an optical sensor, a voice input circuit, or the like. The input interface 31 may be constituted of a tablet terminal and the like capable of communicating with the processing circuitry 34 in a wireless manner. The input interface 31 may also be circuitry that receives the input operation from the user by motion capture. By way of example, the input interface 31 can receive a body motion, a line of sight, and the like of the user as an input operation by processing a signal acquired via a tracker or an acquired image of the user. The input interface 31 does not necessarily include a physical operation component such as a mouse and a keyboard. For example, the input interface 31 may be processing circuitry for an electric signal that receives an electric signal corresponding to the input operation from an external input appliance that is disposed separately from a main body of the medical image processing apparatus 30, and outputs the electric signal to the main body of the medical image processing apparatus 30.

The display 32 displays various kinds of information. For example, the display 32 displays the X-ray image subjected to processing performed by the processing circuitry (described later). For example, the display 32 also displays a graphical user interface (GUI) for receiving various instructions, settings, and the like from the user via the input interface 31. For example, the display 32 is a liquid crystal display or a cathode ray tube (CRT) display. The display 32 may be a desktop type, or may be configured by a tablet terminal and the like capable of communicating with the main body of the medical image processing apparatus 30 in a wireless manner.

Regarding FIG. 1, the medical image processing apparatus 30 is assumed to include the display 32. Alternatively, the medical image processing apparatus 30 may include a projector in place of or in addition to the display 32. The projector can perform projection on a screen, a wall, a floor, a body surface of the subject P1, and the like under control by the processing circuitry 34. By way of example, the projector can perform projection on an optional plane, object, space, and the like by projection mapping.

The memory 33 stores various kinds of data. For example, the memory 33 stores the X-ray images before and after the processing performed by the processing circuitry 34 (described later). The memory 33 also stores a computer program by which a circuit included in the medical image processing apparatus 30 implements a function thereof. For example, the memory 33 is implemented by a semiconductor memory element such as a random access memory (RAM) and a flash memory, a hard disk, or an optical disc. Alternatively, the memory 33 may be implemented by a server group (cloud) connected to the medical image processing apparatus 30 via a network.

The processing circuitry 34 controls an operation of the entire medical image processing apparatus 30 by executing a control function 34a, an acquisition function 34b, a processing function 34c, and an output function 34d. The acquisition function 34b is an example of an acquisition unit. The processing function 34c is an example of a processing unit. The output function 34d is an example of an output unit.

For example, the processing circuitry 34 controls various functions such as the acquisition function 34b, the processing function 34c, and the output function 34d based on the input operation received from the user via the input interface 31 by reading out a computer program corresponding to the control function 34a from the memory 33 to be executed.

For example, the processing circuitry 34 also acquires the X-ray image of the subject P1 by reading out a computer program corresponding to the acquisition function 34b from the memory 33 to be executed. For example, the processing circuitry 34 performs processing on the X-ray image by reading out a computer program corresponding to the processing function 34c from the memory 33 to be executed. Additionally, for example, the processing circuitry 34 outputs the X-ray image subjected to processing performed by the processing function 34c by reading out a computer program corresponding to the output function 34d from the memory 33 to be executed. Details about the processing performed by the acquisition function 34b, the processing function 34c, and the output function 34d will be described later.

In the medical image processing apparatus 30 illustrated in FIG. 1, each of the processing functions is stored in the memory 33 in a form of a computer-executable program. The processing circuitry 34 is a processor that implements a function corresponding to each computer program by reading out and executing the computer program from the memory 33. In other words, the processing circuitry 34 that has read out the computer program is assumed to have a function corresponding to the read-out computer program.

Regarding FIG. 1, it is assumed that the single processing circuitry 34 implements the control function 34a, the acquisition function 34b, the processing function 34c, and the output function 34d. Alternatively, the processing circuitry 34 may be configured by combining a plurality of independent processors, and each of the processors may execute a computer program to implement a function. The respective processing functions of the processing circuitry 34 may be implemented by being appropriately distributed or integrated with each other in a single processing circuit or a plurality of processing circuits.

The processing circuitry 34 may also implement a function by using a processor of an external device connected via the network NW. For example, the processing circuitry 34 implements the respective functions illustrated in FIG. 1 by reading out a computer program corresponding to each function from the memory 33 to be executed, and using a server group (cloud) connected to the medical image processing apparatus 30 via the network NW as a calculation resource.

Figure 2:
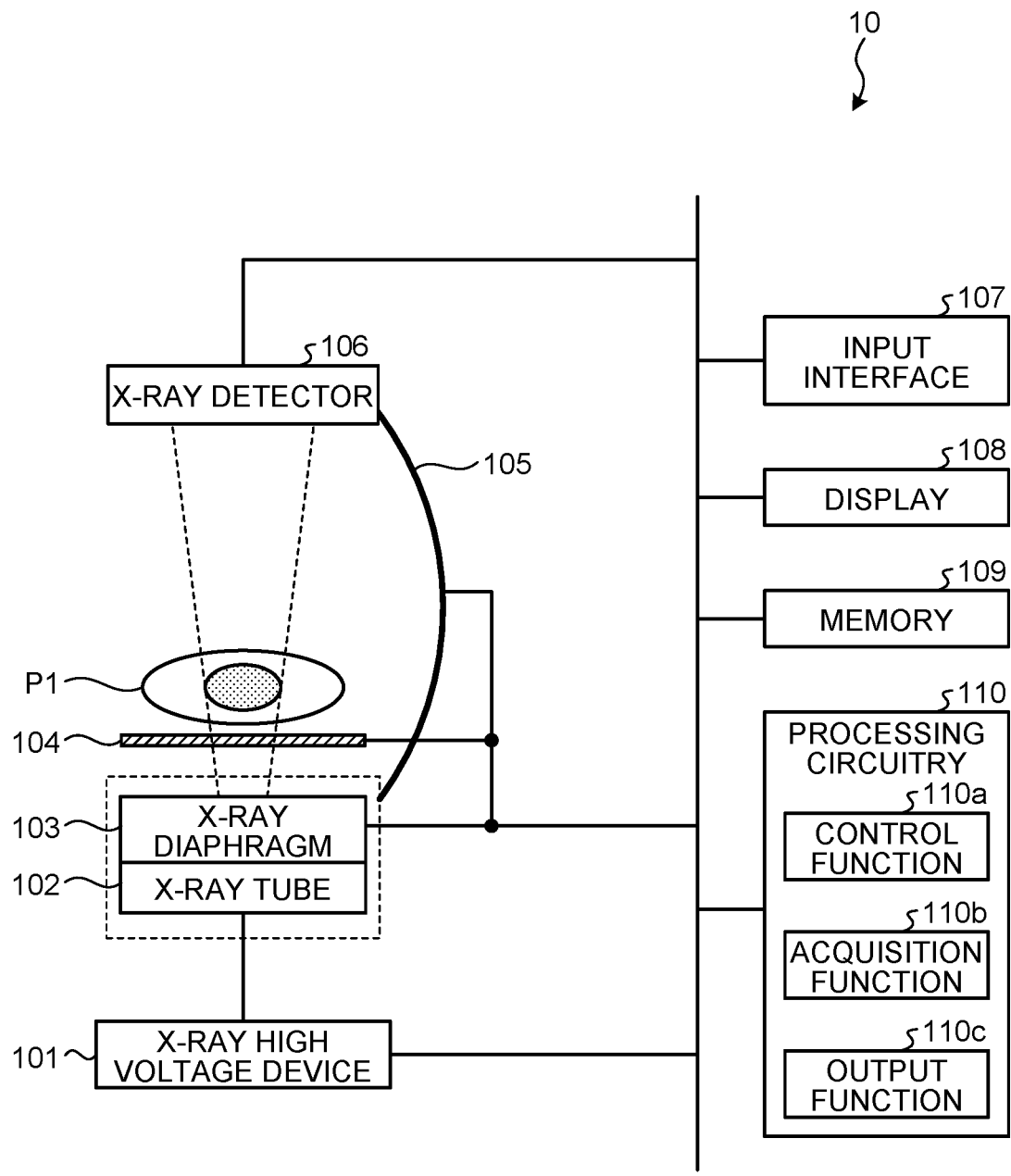
FIG. 2 is a block diagram illustrating an example of a configuration of an X-ray diagnostic apparatus according to the first embodiment.

Next, the following describes the X-ray diagnostic apparatus 10 with reference to FIG. 2. FIG. 2 is a block diagram illustrating an example of a configuration of the X-ray diagnostic apparatus 10 according to the first embodiment. As illustrated in FIG. 2, the X-ray diagnostic apparatus 10 includes an X-ray high voltage device 101, an X-ray tube 102, an X-ray diaphragm 103, a tabletop 104, a C-arm 105, an X-ray detector 106, an input interface 107, a display 108, a memory 109, and processing circuitry 110.

The X-ray high voltage device 101 supplies a high voltage to the X-ray tube 102 under control by the processing circuitry 110. For example, the X-ray high voltage device 101 includes electric circuitry such as a transformer and a rectifier, and includes a high voltage generation device that generates a high voltage to be applied to the X-ray tube 102, and an X-ray control device that controls an output voltage corresponding to X-rays emitted from the X-ray tube 102. The high voltage generation device may be a transformer type, or may be an inverter type.

The X-ray tube 102 is a vacuum tube including a cathode (filament) that generates thermoelectrons, and an anode (target) that generates X-rays when being collided with the thermoelectron. The X-ray tube 102 generates X-rays by emitting thermoelectrons from the cathode toward the anode by using the high voltage supplied from the X-ray high voltage device 101.

The X-ray diaphragm 103 includes a collimator that narrows an irradiation range of the X-rays generated by the X-ray tube 102, and a filter that adjusts the X-rays radiated from the X-ray tube 102.

The collimator in the X-ray diaphragm 103 includes, for example, four slidable diaphragm blades. The collimator slides the diaphragm blades to narrow the X-rays generated by the X-ray tube 102, and irradiates the subject P1 with the X-rays. The diaphragm blade is a plate member constituted of lead and the like, and disposed in the vicinity of an X-ray irradiation port of the X-ray tube 102 to adjust the irradiation range of the X-rays.

The filter in the X-ray diaphragm 103 changes radiation quality of the X-rays to be transmitted due to a material or a thickness thereof for the purpose of reducing an exposure dose for the subject P1 and improving image quality of the X-ray image, and reduces a soft ray component that is easily absorbed by the subject P1, or reduces a high energy component that causes deterioration in contrast of the X-ray image. The filter changes the dose and the irradiation range of the X-rays due to a material, a thickness, a position, and the like thereof, and attenuates the X-rays so that the X-rays emitted from the X-ray tube 102 to the subject P1 are distributed in a predetermined manner.

For example, the X-ray diaphragm 103 includes a driving mechanism such as a motor and an actuator, and controls irradiation of X-rays by causing the driving mechanism to operate under control by the processing circuitry 110 (described later). For example, the X-ray diaphragm 103 adjusts an opening of the diaphragm blades of the collimator to control the irradiation range of the X-rays emitted to the subject P1 by applying a driving voltage to the driving mechanism corresponding to a control signal received from the processing circuitry 110. For example, the X-ray diaphragm 103 adjusts a position of the filter to control dose distribution of the X-rays emitted to the subject P1 by applying the driving voltage to the driving mechanism corresponding to the control signal received from the processing circuitry 110.

The tabletop 104 is a bed on which the subject P1 is placed, and disposed on a table (not illustrated). The subject P1 is not included in the X-ray diagnostic apparatus 10. For example, the table includes a driving mechanism such as a motor and an actuator, and controls movement and inclination of the tabletop 104 by causing the driving mechanism to operate under control by the processing circuitry 110 (described later). For example, the table causes the tabletop 104 to move or incline by applying the driving voltage to the driving mechanism corresponding to the control signal received from the processing circuitry 110.

The C-arm 105 holds the X-ray tube 102 and the X-ray diaphragm 103, and the X-ray detector 106 to be opposed to each other across the subject P1. For example, the C-arm 105 includes a driving mechanism such as a motor and an actuator, and rotates or moves by causing the driving mechanism to operate under control by the processing circuitry 110 (described later). For example, the C-arm 105 rotates and moves the X-ray tube 102, the X-ray diaphragm 103, and the X-ray detector 106 with respect to the subject P1 by applying a driving voltage to the driving mechanism corresponding to the control signal received from the processing circuitry 110, and controls an irradiation position or an irradiation angle of the X-rays. FIG. 2 exemplifies a case in which the X-ray diagnostic apparatus 10 is a single plane system, but the embodiment is not limited thereto. The X-ray diagnostic apparatus 10 may also be a biplane system.

The X-ray detector 106 is, for example, an X-ray flat panel detector (FPD) including detection elements arranged in a matrix. The X-ray detector 106 detects the X-rays that are emitted from the X-ray tube 102 and transmitted through the subject P1, and outputs detection signals corresponding to a dose of the detected X-rays to the processing circuitry 110. The X-ray detector 106 may be a detector of an indirect conversion type including a grid, a scintillator array, and an optical sensor array, or may be a detector of a direct conversion type including a semiconductor element that converts incident X-rays into electric signals.

The input interface 107 can be configured similarly to the input interface 31 described above. For example, the input interface 107 receives various input operations from the user, and converts the received input operations into electric signals to be output to the processing circuitry 110.

The display 108 can be configured similarly to the display 32 described above. For example, the display 108 displays the X-ray image acquired from the subject P1 under control by the processing circuitry 110. The X-ray diagnostic apparatus 10 may also include a projector in place of or in addition to the display 108.

The memory 109 can be configured similarly to the memory 33 described above. For example, the memory 109 stores the X-ray images acquired from the subject P1, or stores a computer program by which circuitry included in the X-ray diagnostic apparatus 10 implements a function thereof.

The processing circuitry 110 executes a control function 110a, an acquisition function 110b, and an output function 110c to control an operation of the entire X-ray diagnostic apparatus 10. The acquisition function 110b is an example of an acquisition unit. The output function 110c is an example of an output unit.

For example, the processing circuitry 110 controls various functions such as the acquisition function 110b and the output function 110c by reading out a computer program corresponding to the control function 110a from the memory 109 to be executed based on an input operation received from the user via the input interface 107.

For example, the processing circuitry 110 acquires the X-ray images from the subject P1 by reading out a computer program corresponding to the acquisition function 110b from the memory 109 to be executed. Furthermore, the processing circuitry 110 outputs the X-ray images acquired from the subject P1 by reading out a computer program corresponding to the output function 110c from the memory 109 to be executed. Details about processing performed by the acquisition function 110b and the output function 110c will be described later.

In the X-ray diagnostic apparatus 10 illustrated in FIG. 2, each of the processing functions is stored in the memory 109 in a form of a computer-executable program. The processing circuitry 110 is a processor that implements a function corresponding to each computer program by reading out and executing the computer program from the memory 109. In other words, the processing circuitry 110 that has read out the computer program is assumed to have the function corresponding to the read-out computer program.

Regarding FIG. 2, it is assumed that the single processing circuitry 110 implements the control function 110a, the acquisition function 110b, and the output function 110c. Alternatively, the processing circuitry 110 may be configured by combining a plurality of independent processors, and each of the processors may execute a computer program to implement the function. The respective processing functions of the processing circuitry 110 may be implemented by being appropriately distributed or integrated with each other in a single processing circuit or a plurality of processing circuits.

The processing circuitry 110 may also implement the function by using a processor of an external device connected via the network NW. For example, the processing circuitry 110 implements the respective functions illustrated in FIG. 2 by reading out a computer program corresponding to each function from the memory 109 to be executed, and using a server group connected to the X-ray diagnostic apparatus 10 via the network NW as a calculation resource.

The configuration example of the medical image processing system 1 has been described above. With this configuration, the medical image processing apparatus 30 in the medical image processing system 1 improves visibility of a device inserted into the body of the subject P1 by processing performed by the processing circuitry 34.

First, the following describes acquisition of the X-ray images from the subject P1. For example, while intravascular treatment is performed by inserting a device into the body of the subject P1, the acquisition function 110b acquires the X-ray image including the device in an imaging range thereof over time. In this case, the imaging range may be set by the user such as a doctor who performs the intravascular treatment, or may be automatically set by the acquisition function 110b based on patient information and the like.

Specifically, the acquisition function 110b controls the irradiation range of the X-rays emitted to the subject P1 by controlling an operation of the X-ray diaphragm 103 and adjusting the opening of the diaphragm blades included in the collimator. The acquisition function 110b also controls the dose distribution of the X-rays by controlling an operation of the X-ray diaphragm 103 and adjusting the position of the filter. The acquisition function 110b also rotates or moves the C-arm 105 by controlling an operation of the C-arm 105. Furthermore, for example, the acquisition function 110b moves or inclines the tabletop 104 by controlling an operation of the table. That is, the acquisition function 110b controls the imaging range or the imaging angle of the X-ray images to be acquired by controlling operations of mechanical systems such as the X-ray diaphragm 103, the C-arm 105, and the tabletop 104.

The acquisition function 110b also controls ON/OFF and the dose of the X-rays emitted to the subject P1 by controlling the X-ray high voltage device 101 and adjusting the voltage supplied to the X-ray tube 102. The acquisition function 110b also generates the X-ray image based on the detection signal received from the X-ray detector 106. In this case, the acquisition function 110b may perform various kinds of image processing on the generated X-ray image. For example, the acquisition function 110b can perform noise reduction processing using an image processing filter, or scattered ray correction on the generated X-ray image.

The device inserted into the body of the subject P1 typically has a wire shape. Examples of such a wire-shaped device include a catheter and a guide wire used for intravascular treatment. For example, in Percutaneous Coronary Intervention (PCI), the user such as a doctor operates a guide wire inserted into the body of the subject P1 to move to a lesion. In this case, the lesion is, for example, a constriction of a blood vessel such as Chronic Total Occlusion (CTO). In such a case, the acquisition function 110b acquires the X-ray images including a distal end of the guide wire in the imaging range thereof over time. When a distal end position of the guide wire is moved, the acquisition function 110b can continuously acquire the X-ray images while appropriately adjusting the imaging range to follow the distal end position of the guide wire.

Next, the acquisition function 34b acquires the X-ray images acquired by the X-ray diagnostic apparatus 10 via the network NW. For example, first, the output function 110c transmits the X-ray images acquired by the acquisition function 110b to an image storage device via the network NW. In this case, the acquisition function 34b can acquire the X-ray images from the image storage device via the network NW. Examples of such an image storage device include a server of a Picture Archiving Communication System (PACS). Alternatively, the acquisition function 34b may acquire the X-ray images directly from the X-ray diagnostic apparatus 10 without using another device.

Next, the processing function 34c performs processing for suppressing movement of the device on the X-ray image. That is, the device may be moved due to influence of heartbeat, respiration, or the like of the subject P1 depending on a treatment target site. In a case in which the acquired X-ray image is displayed as it is, the device may be moved on the X-ray image, and it may be difficult for the user to visually recognize the device in some cases. Thus, the processing function 34c performs processing of suppressing movement of the device on the X-ray image before being displayed.

Figure 3:
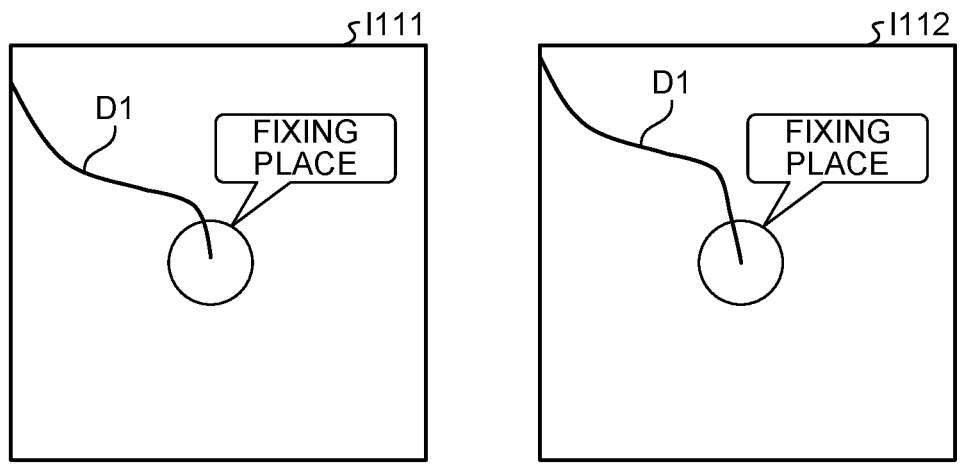
FIG. 3 is a diagram illustrating an example of processing of a processing function according to the first embodiment.

The following describes an example of the processing performed by the processing function 34c with reference to FIG. 3. FIG. 3 is a diagram illustrating an example of the processing of the processing function 34c according to the first embodiment. Each of an X-ray image I111 and an X-ray image I112 in FIG. 3 is an X-ray image including a device D1 inserted into the body of the subject P1 in an imaging range thereof. For example, the X-ray image I112 is an X-ray image of a frame next to the X-ray image I111.

In a case illustrated in FIG. 3, the processing function 34c performs processing of suppressing movement of a distal end position of the device D1 on the image. Specifically, first, the processing function 34c specifies the distal end position of the device D1 in each of the X-ray image I111 and the X-ray image I112. Next, the processing function 34c performs processing on the X-ray image I112 so that distal end positions of the device D1 on the images match each other between the X-ray image I111 and the X-ray image I112. For example, the processing function 34c translates the X-ray image I112 corresponding to the distal end position of the device D1 specified in the X-ray image I111. The output function 34d causes the display 32 to successively display the X-ray image I111 and the X-ray image I112 after the processing. In this case, the distal end position of the device D1 is fixed on the image, so that the user is enabled to observe the device D1 more easily.

However, in the case illustrated in FIG. 3, the distal end position of the device D1 does not move on the image even when the user moves the device D1 forward or backward. That is, fixed display as illustrated in FIG. 3 is useful for observing the distal end or a peripheral region of the device D1, but the movement of the device D1 is difficult to be recognized when the device D1 is operated in some cases.

Figure 4:
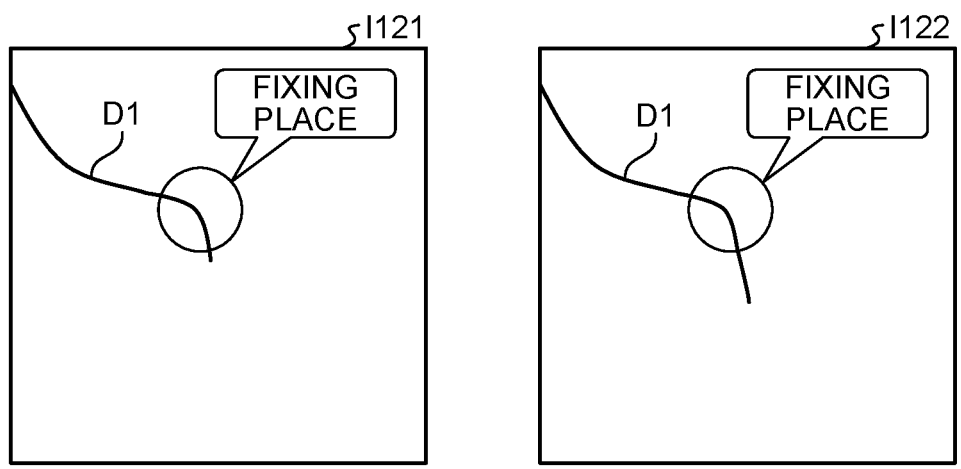
FIG. 4 is a diagram illustrating an example of processing of a processing function according to the first embodiment.

Thus, as illustrated in FIG. 4, the processing function 34c performs processing of suppressing movement of a characteristic portion characterized in a shape that is positioned distant from the distal end of the device D1 to further improve visibility of the device D1. FIG. 4 is a diagram illustrating an example of the processing of the processing function 34c according to the first embodiment. Each of an X-ray image I121 and an X-ray image I122 in FIG. 4 is an X-ray image including the device D1 inserted into the body of the subject P1 in the imaging range thereof. For example, the X-ray image I122 is an X-ray image of a frame next to the X-ray image I121.

The device D1 is inserted into the blood vessel of the subject P1, and deformed along the shape of the blood vessel. That is, the device D1 is inserted into the blood vessel to be deformed, and includes a portion characterized in a shape. In the following description, the portion of the device D1 characterized in the shape thereof is also referred to as a characteristic portion, the portion generated in the device D1 that is inserted into the blood vessel. The characteristic portion is, for example, a portion having a large curvature in the wire-shaped device D1. That is, in the case illustrated in FIG. 4, the processing function 34c performs processing of suppressing movement of the characteristic portion between the X-ray image I121 and the X-ray image I122.

Figure 5:
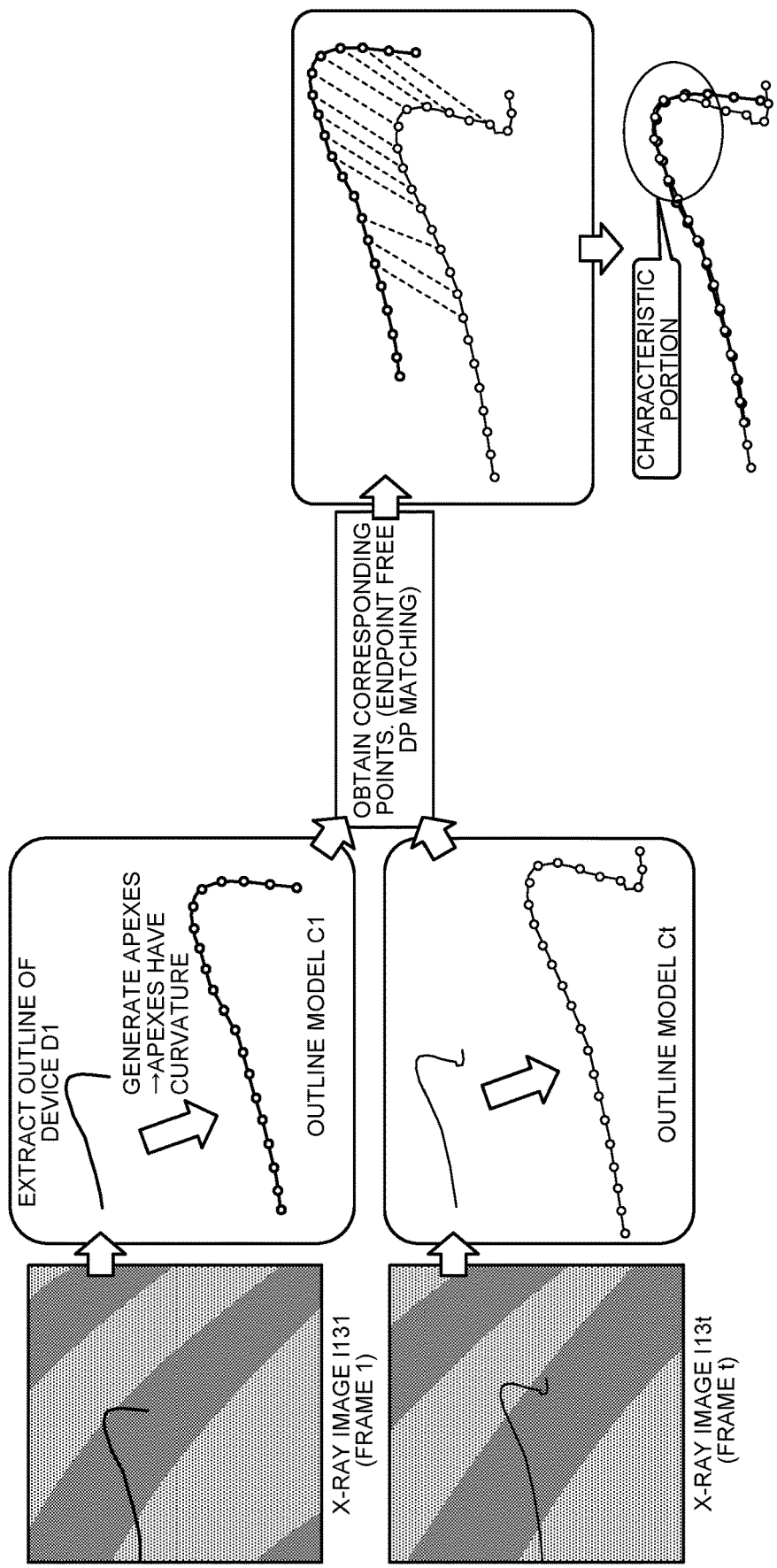
FIG. 5 is a diagram illustrating an example of matching processing according to the first embodiment.

For example, the processing function 34c can perform the processing of suppressing movement of the characteristic portion by performing matching processing between the images. The following describes an example of the matching processing between the images with reference to FIG. 5. FIG. 5 is a diagram illustrating an example of the matching processing according to the first embodiment.

Regarding FIG. 5, endpoint free Dynamic Programming (DP) matching is described as an example of the matching processing between the images. Regarding FIG. 5, described is a case in which an X-ray image I131 of a frame 1 is assumed to be a reference frame, and the processing of suppressing movement of the characteristic portion is performed for an X-ray image I13t of a frame t subsequent to the frame 1. That is, in the case illustrated in FIG. 5, the processing function 34c suppresses movement of the characteristic portion by performing matching processing between the X-ray image I131 and the X-ray image I13t.

Specifically, first, the processing function 34c extracts an outline of the device D1 from the X-ray image I131. Next, the processing function 34c generates a plurality of apexes on the extracted outline to generate an outline model C1. Similarly, the processing function 34c extracts the outline of the device D1 from the X-ray image I13t to generate an outline model Ct.

Next, the processing function 34c obtains corresponding points between the X-ray image I131 and the X-ray image I13t. For example, the processing function 34c defines a cost corresponding to correspondence between the apexes in the outline model C1 and the apexes in the outline model Ct, and obtains the corresponding points by minimizing the cost. In this case, for example, the cost can be defined in accordance with a difference between characteristic amounts of the respective corresponding apexes.

For example, the processing function 34c adds, to each of the apexes in the outline model C1 and the outline model Ct, a curvature of the device D1 at a present position and a surrounding pixel value as the characteristic amount. The surrounding pixel value is an average value of pixel values within a predetermined range from the apex, for example. The processing function 34c can obtain the corresponding points so that the apexes having substantially the same characteristic amount have a correspondence relation by defining the cost in accordance with the difference between the characteristic amounts, and solving a minimization problem for minimizing the cost.

Additionally, the processing function 34c aligns the X-ray image I13t with the X-ray image I131 based on the correspondence relation between the apexes. For example, the processing function 34c calculates a rotation/translation matrix W using singular value decomposition and the like based on the correspondence relation between the apexes. The processing function 34c then translates and rotates the X-ray image I13t by applying the rotation/translation matrix W thereto, and aligns the X-ray image I13t with the X-ray image I131.

In calculating the rotation/translation matrix W, the curvature of the respective apexes is used as the characteristic amount. The curvature is fixed to be substantially zero at a straight portion of the device D1, but the characteristic portion of the device D1 at which the curvature is changed largely contributes to calculation of the rotation/translation matrix W. Thus, in a case of aligning the X-ray image I13t with the X-ray image I131 using the rotation/translation matrix W, as illustrated in FIG. 5, characteristic portions are aligned with each other with priority, and movement thereof is suppressed. The output function 34d then causes the display 32 to successively display the X-ray image I131 and the X-ray image I13t to which the rotation/translation matrix W has been applied.

The processing function 34c may generate the outline model C1 for the entire device D1 appearing in the X-ray image I131, or may generate the outline model C1 for part of the device D1. For example, the processing function 34c generates the outline model C1 for a portion of a predetermined length from the distal end of the device D1. For example, the processing function 34c generates the apexes at regular intervals from the distal end of the device D1 as needed, and ends the generation of the apexes at the time when the number of apexes reaches a predetermined number to generate the outline model C1. Alternatively, for example, the processing function 34c generates the apexes at regular intervals from the distal end of the device D1 as needed, and ends the generation of the apexes at the time when distribution of the characteristic amounts of the generated apexes exceeds predetermined distribution to generate the outline model C1. The same applies to the outline model Ct.

FIG. 5 illustrates a case of generating the apexes at substantially regular intervals in the outline model, but the intervals between the apexes may be appropriately changed. For example, the processing function 34c may dispose the apexes densely for a portion having a large curvature in the outline model, and may dispose the apexes sparsely for a portion having a small curvature.

Regarding FIG. 5, it is assumed that the corresponding points are obtained, but the embodiment is not limited thereto. For example, the processing function 34c creates a curved line graph representing change in the characteristic amount such as the curvature along the outline model for each of the X-ray images. The processing function 34c can align the X-ray images with each other so as to suppress movement of the characteristic portion by optimizing a positional relation between curved line graphs.

FIG. 5 exemplifies the case in which one characteristic portion appears on each image, but the embodiment is not limited thereto. The embodiment can also be applied to a case in which a plurality of characteristic portions appear on each image. The processing function 34c may also generate the outline model C1 and the outline model Ct corresponding to the number of characteristic portions. For example, the processing function 34c generates the apexes at regular intervals from the distal end of the device D1 as needed, and ends the generation of the apexes at the time of determining that a predetermined number of characteristic portions are included therein to generate the outline model C1 and the outline model Ct.

That is, the processing function 34c can control the number of characteristic portions to be used. In performing the processing of suppressing movement of the characteristic portion, as a larger number of characteristic portions are considered, accuracy is improved, but a calculation amount is increased. The processing function 34c may allow the user to adjust the number of characteristic portions to be used, or may automatically adjust the number of characteristic portions to be used in accordance with processing capacity of the medical image processing apparatus 30, a frame rate of the X-ray image to be acquired, and the like.

Figure 6:
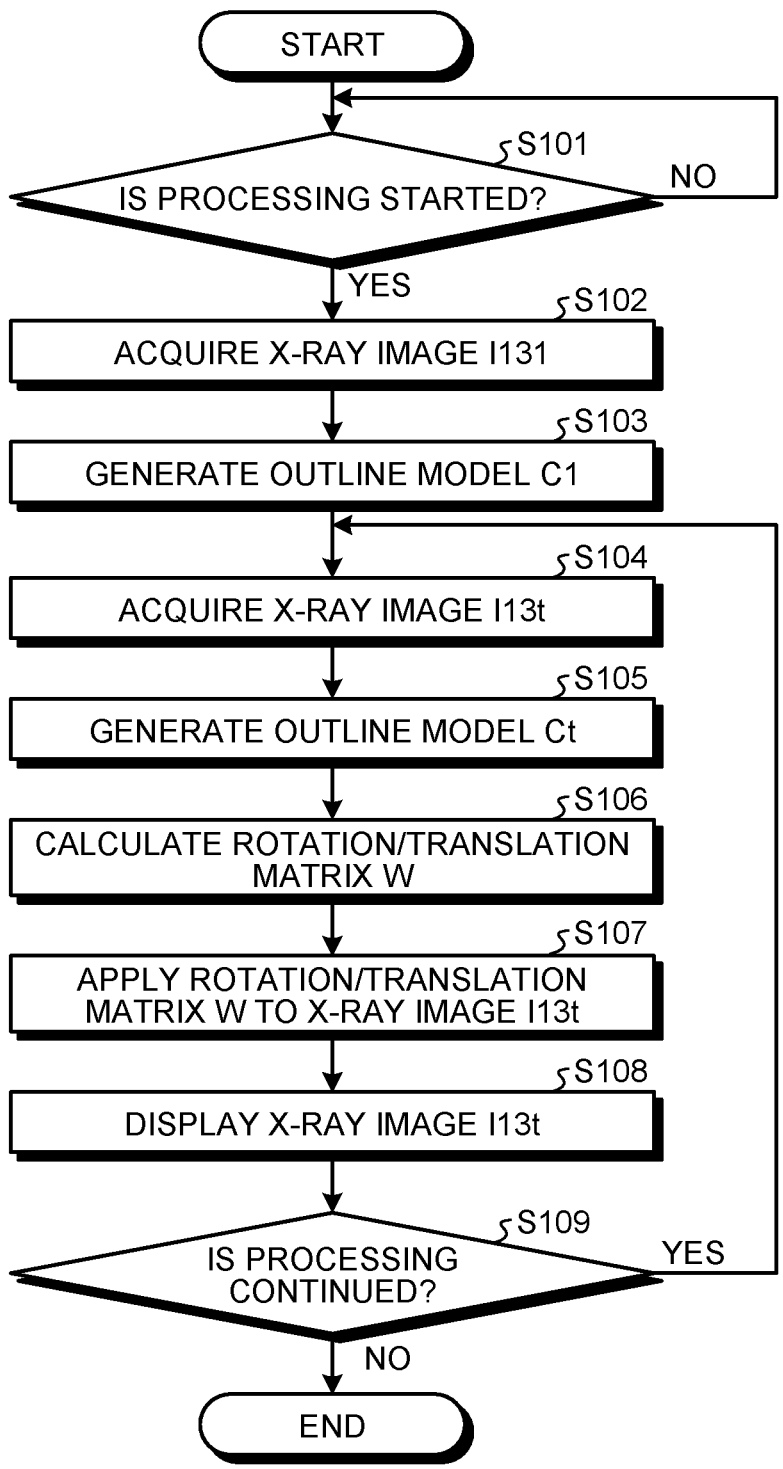
FIG. 6 is a flowchart for explaining a series of procedures of processing performed by a medical image processing apparatus according to the first embodiment.

Next, the following describes an example of a processing procedure performed by the medical image processing apparatus 30 with reference to FIG. 6. FIG. 6 is a flowchart for explaining a series of procedures of processing performed by the medical image processing apparatus 30 according to the first embodiment. Step S101, Step S102, and Step S104 are steps corresponding to the acquisition function 34b. Step S103, Step S105, Step S106, and Step S107 are steps corresponding to the processing function 34c. Step S108 and Step S109 are steps corresponding to the output function 34d.

First, the processing circuitry 34 determines whether to start the processing of suppressing movement of the device D1 (Step S101). For example, even after the device D1 is inserted into the body of the subject P1, the processing of suppressing movement of the device D1 is not required in some cases depending on the position of the device D1. For example, in the PCI, the device D1 is inserted from a femoral artery of the subject P1, and moves in the blood vessel toward a heart. In this case, the processing of suppressing movement of the device D1 is not required when the device D1 is positioned at a leg of the subject P1, and is required when the device D1 approaches the heart and is influenced by heartbeat. Thus, the processing circuitry 34 can determine to start the processing of suppressing movement of the device D1 when the device D1 reaches the vicinity of the heart.

Determination at Step S101 may be performed by receiving an input operation from the user such as a doctor, or may be automatically performed by the processing circuitry 34 by analyzing the position of the device D1. If the processing is not started (No at Step S101), the processing circuitry 34 is caused to be in a standby state. If the processing is started (Yes at Step S101), the processing circuitry 34 advances the process to Step S102.

Next, the processing circuitry 34 acquires the X-ray image I131 (Step S102), and generates the outline model C1 (Step S103). The processing circuitry 34 also acquires the X-ray image I13t (Step S104), and generates the outline model Ct (Step S105). The X-ray image I13t is an X-ray image of a frame subsequent to the X-ray image I131. The X-ray image I13t may be an X-ray image of a frame immediately after the X-ray image I131, or may be an X-ray image several frames after the X-ray image I131.

Next, the processing circuitry 34 calculates the rotation/translation matrix W (Step S106). For example, the processing circuitry 34 performs endpoint free DP matching between the outline model C1 and the outline model Ct, and obtains the corresponding points to calculate the rotation/translation matrix W. The processing circuitry 34 applies the calculated rotation/translation matrix W to the X-ray image I13t (Step S107). Due to this, the X-ray image I13t is aligned with the X-ray image I131, and movement of the characteristic portion characterized in the shape of the device D1 is suppressed in the X-ray image I131 and the X-ray image I13t.

The processing circuitry 34 causes the display 32 to display the X-ray image I13t to which the rotation/translation matrix W is applied (Step S108). That is, at Step S108, the processing circuitry 34 causes the display 32 to display the X-ray image in which movement of the characteristic portion is suppressed.

Next, the processing circuitry 34 determines whether to continue the processing of suppressing movement of the device D1 (Step S109). If the processing is continued (Yes at Step S109), the process proceeds to Step S104 again. For example, in a case in which the X-ray image I13t of the frame t is acquired and the processing of suppressing movement of the device D1 is performed, and the process proceeds from Step S109 to Step S104 again, the processing circuitry 34 acquires the X-ray image of a frame (t+1), and can perform the processing of suppressing movement of the device D1 again. On the other hand, if the processing of suppressing movement of the device D1 is not continued (No at Step S109), the processing circuitry 34 ends the processing.

In a processing flow illustrated in FIG. 6, the X-ray image I131 acquired at Step S102 becomes the reference frame. That is, in the processing flow illustrated in FIG. 6, the processing of suppressing movement of the device D1 is performed by using the characteristic portion characterized in the shape of the device D1 at the time when the X-ray image I131 is acquired. However, there may be a case in which the X-ray image I131 is not preferable as the reference frame. For example, there may be a case in which most part of the device D1 is positioned at a straight portion of the blood vessel at the time when the X-ray image I131 is acquired, and the characteristic portion is not generated in the device D1. Additionally, for example, there may be a case in which body motion of the subject P1 is present at the time when the X-ray image I131 is acquired, and noise is generated in the X-ray image I131.

Thus, the processing circuitry 34 may appropriately change the reference frame. For example, the processing circuitry 34 sets the reference frame again by causing the display 32 to display the X-ray images corresponding to a plurality of frames that are acquired most recently, and receiving a selection operation for selecting the X-ray image as the reference frame from the user. Additionally, for example, the processing circuitry 34 receives an input operation for changing the reference frame from the user, and sets the X-ray image that is acquired most recently as the reference frame again. The processing circuitry 34 can perform processing subsequent to Step S103 in FIG. 6 using the X-ray image of the reference frame that has been set again as the X-ray image I131.

While the processing of FIG. 6 is performed, for example, a working angle may be changed in some cases because the C-arm 105 is operated by the user. That is, an imaging angle may be changed between the X-ray image I131 and the X-ray image I13t. In such a case, the shape of the device D1 may be changed on the image, and the processing of suppressing movement of the characteristic portion cannot be performed in some cases.

Thus, the processing circuitry 34 may automatically end the processing of suppressing movement of the characteristic portion when the imaging angle is changed. Additionally, the processing circuitry 34 may automatically resume the processing of suppressing movement of the characteristic portion when the imaging angle is restored. Alternatively, the processing circuitry 34 may set the reference frame again when the imaging angle is changed.

While the processing of FIG. 6 is performed, the device D1 not only moves forward in the blood vessel but also moves backward (is pulled back) in some cases. In a case in which the device D1 moves backward across a curved part and the like of the blood vessel, the characteristic portion does not appear in the X-ray image I13t in some cases. Thus, in a case in which the device D1 moves backward and the characteristic portion does not appear in the X-ray image I13t, the processing circuitry 34 may automatically end the processing of suppressing movement of the characteristic portion.

Alternatively, in a case in which the device D1 moves backward and the characteristic portion does not appear in the X-ray image I13t, the processing circuitry 34 may continue the processing of suppressing movement of the characteristic portion based on a processing result in the past. For example, influence on movement caused by heartbeat or respiration is found at substantially the same level and periodically in the entire imaging range. Thus, even after the device D1 moves backward and the characteristic portion does not appear in the X-ray image I13t, it is possible to substantially suppress movement of a portion at which the characteristic portion is positioned in the X-ray image I13t by applying the rotation/translation matrix W in the past including the same phases of heartbeat and respiration. For example, each time the rotation/translation matrix W is calculated, the processing circuitry 34 stores, in the memory 33, the rotation/translation matrix W in association with phase information of heartbeat, respiration, and the like of the subject P1. When the device D1 moves backward and the characteristic portion does not appear in the X-ray image I13t, the processing circuitry 34 reads out the rotation/translation matrix W including the same phase from the memory 33, and applies the rotation/translation matrix W to the X-ray image I13t.

There may be other cases in which the corresponding points between the outline model C1 and the outline model Ct cannot be obtained due to various factors. For example, there may be a case in which the device D1 largely moves forward or backward, so that the shape is significantly changed between the outline models, and it becomes difficult to obtain the corresponding points. By way of example, in a case of generating the outline model C1 and the outline model Ct for a portion of a predetermined length from the distal end of the device D1, the outline model C1 and the outline model Ct represent different portions of the device D1 when the device D1 moves forward exceeding the predetermined length, so that the corresponding points between the outline models cannot be obtained. Body motion of the subject P1 is present and noise is generated in the X-ray image I13t at the time when the X-ray image I13t is acquired, so that it may be difficult to obtain the corresponding points.

Thus, in a case in which the corresponding points between the outline model C1 and the outline model Ct cannot be obtained, the processing circuitry 34 may automatically end the processing of suppressing movement of the characteristic portion. For example, the processing circuitry 34 calculates the sum total of distance between the corresponding points and the like as an alignment error as needed, and automatically ends the processing of suppressing movement of the characteristic portion at the time when the alignment error exceeds a threshold. Additionally, for example, the processing circuitry 34 calculates a similarity between the outline models, and automatically ends the processing of suppressing movement of the characteristic portion at the time when the similarity becomes lower than a threshold.

Alternatively, in a case in which the corresponding points between the outline model C1 and the outline model Ct cannot be obtained, the processing circuitry 34 may continue the processing of suppressing movement of the characteristic portion based on a processing result in the past. For example, when the corresponding points between the X-ray image I131 and the X-ray image I13t cannot be obtained, the processing circuitry 34 reads out the rotation/translation matrix W that has been calculated in the past and stored in the memory 33, the rotation/translation matrix W including the same phases of heartbeat, respiration, and the like, and applies the rotation/translation matrix W to the X-ray image I13t.

For example, when the corresponding points between the outline model C1 and the outline model Ct cannot be obtained, the processing circuitry 34 may use the rotation/translation matrix W that is calculated most recently. In the following description, it is assumed that an X-ray image I13(t−1) is acquired in a frame immediately before the X-ray image I13t. In many cases, a time after the X-ray image I13(t−1) is acquired until the X-ray image I13t is acquired is short, and movement between the images is small. Thus, by directly applying the rotation/translation matrix W that is calculated for suppressing movement of the characteristic portion in the X-ray image I13(t−1) to the X-ray image I13t, movement of the characteristic portion in the X-ray image I13t can also be substantially suppressed. Due to this, even in a case in which the corresponding points between the outline model C1 and the outline model Ct cannot be obtained for only one frame in which noise is generated, for example, the processing of suppressing movement of the characteristic portion can be continued.

Alternatively, the processing circuitry 34 may periodically update the reference frame. For example, at the time when pieces of the processing from Step S104 to Step S109 in FIG. 6 are repeated by predetermined number of times, the processing circuitry 34 sets the X-ray image that is acquired most recently as the reference frame again. The processing circuitry 34 performs processing subsequent to Step S103 again by using the X-ray image of the reference frame that is set again as the X-ray image I131. Due to this, the processing circuitry 34 can continue the processing of suppressing movement of the characteristic portion even in a case in which the device D1 moves forward or backward and the shape of the outline model is largely changed, a case in which the shape of the characteristic portion on the image is changed because the working angle is changed, and the like.

As described above, according to the first embodiment, the acquisition function 34b acquires the X-ray images including the device D1 that is inserted into the body of the subject P1. The processing function 34c suppresses movement of the characteristic portion characterized in the shape that is positioned distant from the distal end of the device D1 among the X-ray images. The output function 34d causes the display 32 to display the X-ray images in which movement of the characteristic portion is suppressed. Thus, the medical image processing apparatus 30 according to the first embodiment can improve visibility of the device D1 inserted into the body of the subject P1. That is, the medical image processing apparatus 30 according to the first embodiment can Improve visibility of the X-ray image. By extension, the medical image processing apparatus 30 can reduce a burden on eyes or mental stress of the user, and can facilitate intravascular treatment.

Specifically, the medical image processing apparatus 30 according to the first embodiment enables the user to easily grasp whether the device D1 moves in an intended direction when the user operates the device D1. That is, in a case of performing the processing of suppressing movement of the characteristic portion, the distal end of the device D1 moves on the image in accordance with an operation on the device D1 by the user. Due to this, the user can grasp a movement degree of the device D1, and can perform intravascular treatment more easily.

In a case in which a marker is added to the device D1, the device D1 can be fixedly displayed by detecting markers from the respective X-ray images to be aligned with each other. In this case, the marker is a metal piece having a predetermined shape and size, for example. However, in view of invasiveness with respect to the subject P1 and operability of the device D1, it is preferable not to add the marker to the device D1. In a case in which a target is a narrow blood vessel, the marker cannot be added to the device D1 in some cases. On the other hand, the medical image processing apparatus 30 according to the first embodiment can suppress movement of the characteristic portion characterized in the shape of the device D1 to be displayed irrespective of whether the marker is added to the device D1.

For example, there may be a case in which the processing of suppressing movement of the distal end of the device D1 is preferable, such as a case in which operation of the device D1 has ended, and the user desires to simply observe the vicinity of the distal end of the device D1. Thus, the medical image processing apparatus 30 may switch between the processing of suppressing movement of the characteristic portion and the processing of suppressing movement of the distal end to be performed in accordance with an input operation from the user.

Second Embodiment

The first embodiment has been described above, but various different forms can be employed in addition to the embodiment described above.

For example, in the embodiment described above, as illustrated in FIG. 5, it is assumed that movement of the characteristic portion is suppressed by obtaining the corresponding points by endpoint free DP matching. However, the embodiment is not limited thereto.

Figure 7:
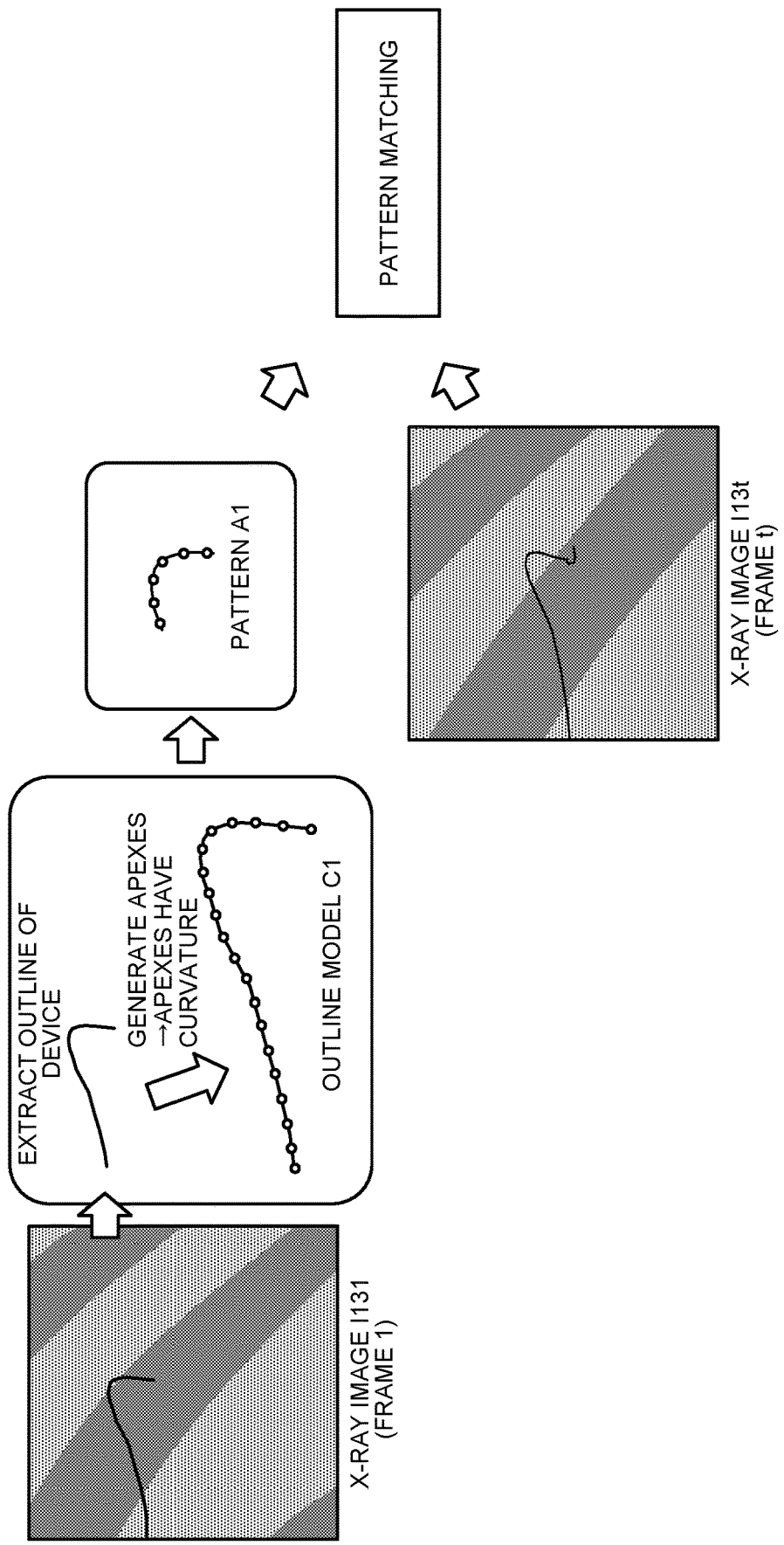
FIG. 7 is a diagram illustrating an example of matching processing according to a second embodiment.

By way of example, the processing function 34c can also suppress movement of the characteristic portion by extracting characteristic portions from the respective X-ray images, and performing matching processing for the characteristic portions among the X-ray images. The following describes a case of performing matching processing for the characteristic portions with reference to FIG. 7. FIG. 7 is a diagram illustrating an example of matching processing according to the second embodiment.

Specifically, first, the processing function 34c extracts the outline of the device D1 from the X-ray image I131 of the frame 1. Next, the processing function 34c generates a plurality of apexes on the extracted outline to generate the outline model C1. The processing function 34c cuts out a portion corresponding to the characteristic portion in the outline model C1 as a pattern A1. For example, the processing function 34c compares a curvature at each apex in the outline model C1 with a threshold, and cuts out a portion corresponding to the apexes at which the curvature exceeds the threshold as the pattern A1.

Next, the processing function 34c performs pattern matching on the X-ray image I13t of the frame t using the pattern A1. Due to this, the processing function 34c specifies a position and orientation of the characteristic portion in the X-ray image I13t. The processing function 34c calculates the rotation/translation matrix W based on the position and orientation of the characteristic portion in the X-ray image I131, and the position and orientation of the characteristic portion in the X-ray image I13t. The processing function 34c translates and rotates the X-ray image I13t by applying the rotation/translation matrix W to the X-ray image I13t, and suppresses movement of the characteristic portion.

In the embodiment described above, it is assumed that the processing of suppressing movement of the characteristic portion is performed for the X-ray image I13t, and the display 32 is caused to display the X-ray image I13t after the processing. However, the embodiment is not limited thereto. For example, the processing circuitry 34 may perform the processing of suppressing movement of the characteristic portion for the X-ray image I13t, generate a synthesized image using the X-ray image I13t after the processing, and cause the display 32 to display the generated synthesized image.

Figure 8:
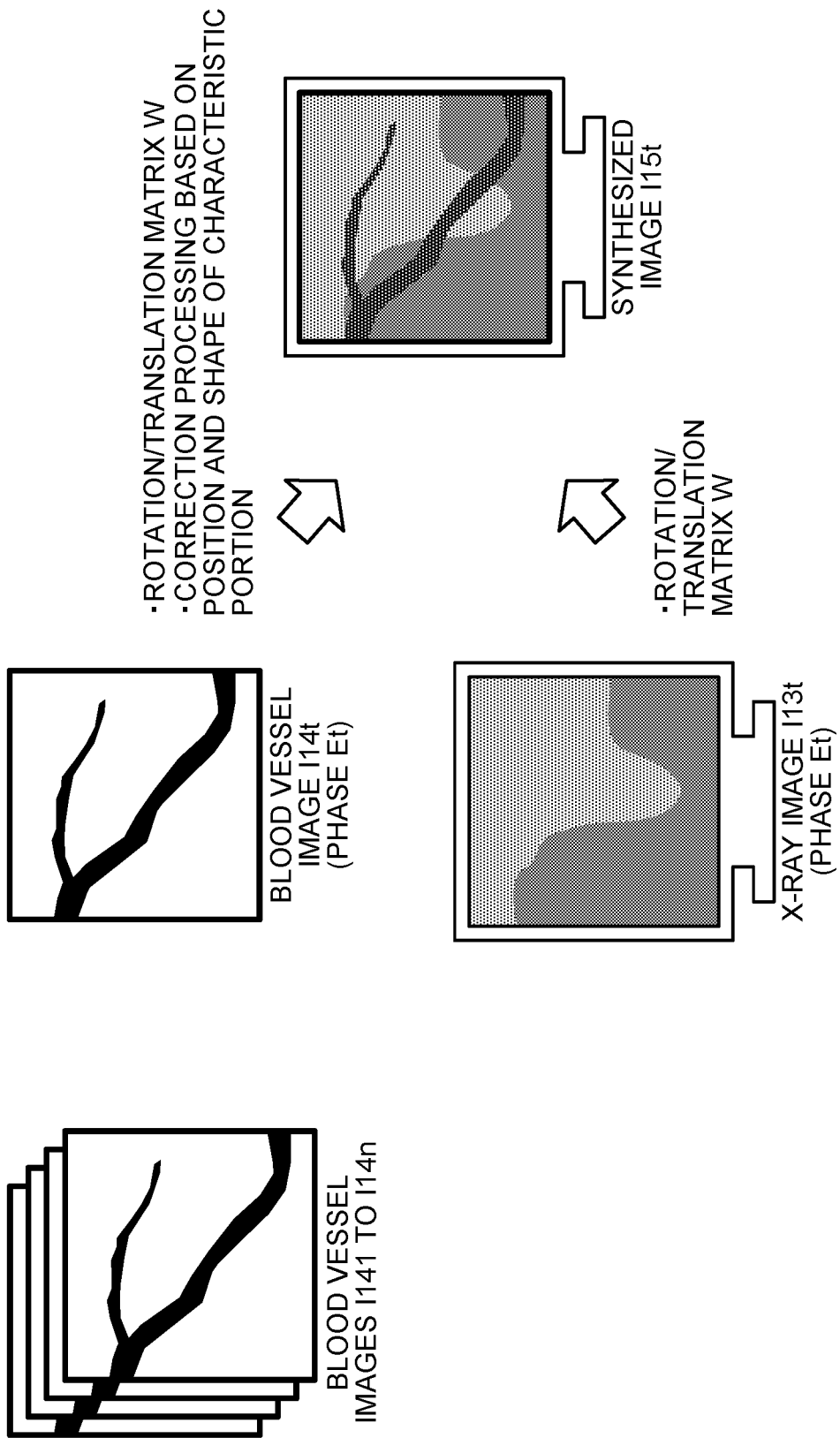
FIG. 8 is a diagram illustrating a display example according to the second embodiment.

The following describes a case of displaying the synthesized image with reference to FIG. 8. FIG. 8 is a diagram illustrating a display example according to the second embodiment. Regarding FIG. 8, described is a case of displaying the synthesized image of the X-ray image I13t and a blood vessel image.

For example, the acquisition function 34b previously acquires the blood vessel image acquired from the subject P1, and causes the memory 33 to store the blood vessel image. By way of example, the blood vessel image can be acquired by imaging the subject P1 in a state in which a contrast medium is injected into his/her blood vessel by the X-ray diagnostic apparatus 10. A type of the contrast medium is not limited. The contrast medium may be a positive contrast medium containing iodine, barium sulfate, and the like as principal components, or may be a gas contrast medium such as carbon dioxide. The contrast medium may be manually injected by the user such as a doctor, or may be automatically injected by an injector disposed on the X-ray diagnostic apparatus 10.

By way of example, the acquisition function 110b acquires a plurality of mask images by repeatedly emitting X-rays before the contrast medium is injected into the blood vessel of the subject P1. The acquisition function 110b also acquires a plurality of contrast images by repeatedly emitting X-rays after the contrast medium is injected into the blood vessel of the subject P1. The acquisition function 110b then performs difference processing between the mask images and the contrast images to generate blood vessel images I141 to I14n illustrated in FIG. 8. Alternatively, the acquisition function 110b may generate the blood vessel images I141 to I14n by performing threshold processing and the like on the contrast images without acquiring the mask images.

For example, in a case of acquiring blood vessel images of coronary arteries of the subject P1, the acquisition function 110b performs electrocardiographic synchronization in the processing of generating the blood vessel images I141 to I14n. For example, the acquisition function 110b acquires the mask images while measuring heartbeat of the subject P1, and attaches phase information to each of the mask images. The acquisition function 110b acquires the contrast images while measuring heartbeat of the subject P1, and attaches the phase information to each of the contrast images. The acquisition function 110b also generates the blood vessel images I141 to I14n by performing difference processing between the mask image and the contrast image of corresponding phases. At this point, the acquisition function 110b can also attach the phase information to each of the blood vessel images I141 to I14n.

The blood vessel images I141 to I14n acquired by the acquisition function 110b are transmitted to the medical image processing apparatus 30 via the network NW. For example, the output function 110c transmits the blood vessel images I141 to I14n to an image storage device such as a PACS server. In this case, the acquisition function 34b can acquire the blood vessel images I141 to I14n from the image storage device. Alternatively, the acquisition function 34b may directly acquire the blood vessel images I141 to I14n from the X-ray diagnostic apparatus 10 without using the image storage device. The acquisition function 34b causes the memory 33 to store the acquired blood vessel images I141 to I14n.

Next, the medical image processing apparatus 30 acquires the X-ray images each including the device inserted into the body of the subject P1 in the imaging range, and performs the processing of suppressing movement of the characteristic portion characterized in the shape that is positioned distant from the distal end of the device D1. For example, the processing function 34c calculates the rotation/translation matrix W by performing matching processing between the X-ray image I131 and the X-ray image I13t by using a method such as endpoint free DP matching illustrated in FIG. 5. For example, the processing function 34c calculates the rotation/translation matrix W by performing matching processing for the characteristic portions between the X-ray image I131 and the X-ray image I13t by using a method such as pattern matching illustrated in FIG. 7. The processing function 34c then applies the calculated rotation/translation matrix W to the X-ray image I13t to suppress movement of the characteristic portion in the X-ray image I13t.

Furthermore, the processing function 34c synthesizes the blood vessel image I14t with the X-ray image I13t. For example, in a case in which the X-ray image I13t is an image acquired in a phase Et, the processing function 34c specifies the blood vessel image I14t of the phase Et among the blood vessel images I141 to I14n to be synthesized with the X-ray image I13t. In this case, the processing function 34c can perform correction processing for the blood vessel image I14t to improve accuracy in synthesis.

For example, the processing function 34c performs correction processing T1 for the blood vessel image I14t based on a result of matching processing between the X-ray image I131 and the X-ray image I13t. That is, both of the X-ray image I13t and the blood vessel image I14t are images acquired in the phase Et, but the rotation/translation matrix W is applied to the X-ray image I13t, so that the position and orientation of the X-ray image I13t is changed. Thus, the processing function 34c can improve accuracy in synthesis of the X-ray image I13t and the blood vessel image I14t by also applying the rotation/translation matrix W to the blood vessel image I14t to change the position and orientation thereof similarly to the X-ray image I13t.

For example, the processing function 34c performs correction processing T2 for the blood vessel image I14t based on the characteristic portion extracted from the X-ray image I13t. That is, the characteristic portion is part of the device D1 inserted into the blood vessel, so that at least the position and the shape of the characteristic portion in the X-ray image I13t are required to match a blood vessel region indicated by the blood vessel image I14t to appropriately synthesize the X-ray image I13t with the blood vessel image I14t. Thus, the processing function 34c corrects the blood vessel image I14t so that the position and the shape of the blood vessel region indicated by the blood vessel image I14t match those of the characteristic portion extracted from the X-ray image I13t. The processing function 34c may perform both of the correction processing T1 and the correction processing T2 described above, or may perform any one of the correction processing T1 and the correction processing T2.

The processing function 34c then generates a synthesized image I15t of the X-ray image I13t and the blood vessel image I14t after the correction processing, and the output function 34d causes the display 32 to display the synthesized image I15t. Due to this, the blood vessel image I14t and the X-ray image I13t are synthesized with high accuracy, and movement of a portion corresponding to the characteristic portion in the blood vessel image I141 is suppressed, so that the user is enabled to grasp a positional relation between the blood vessel and the device D1 more easily.

Figure 9:
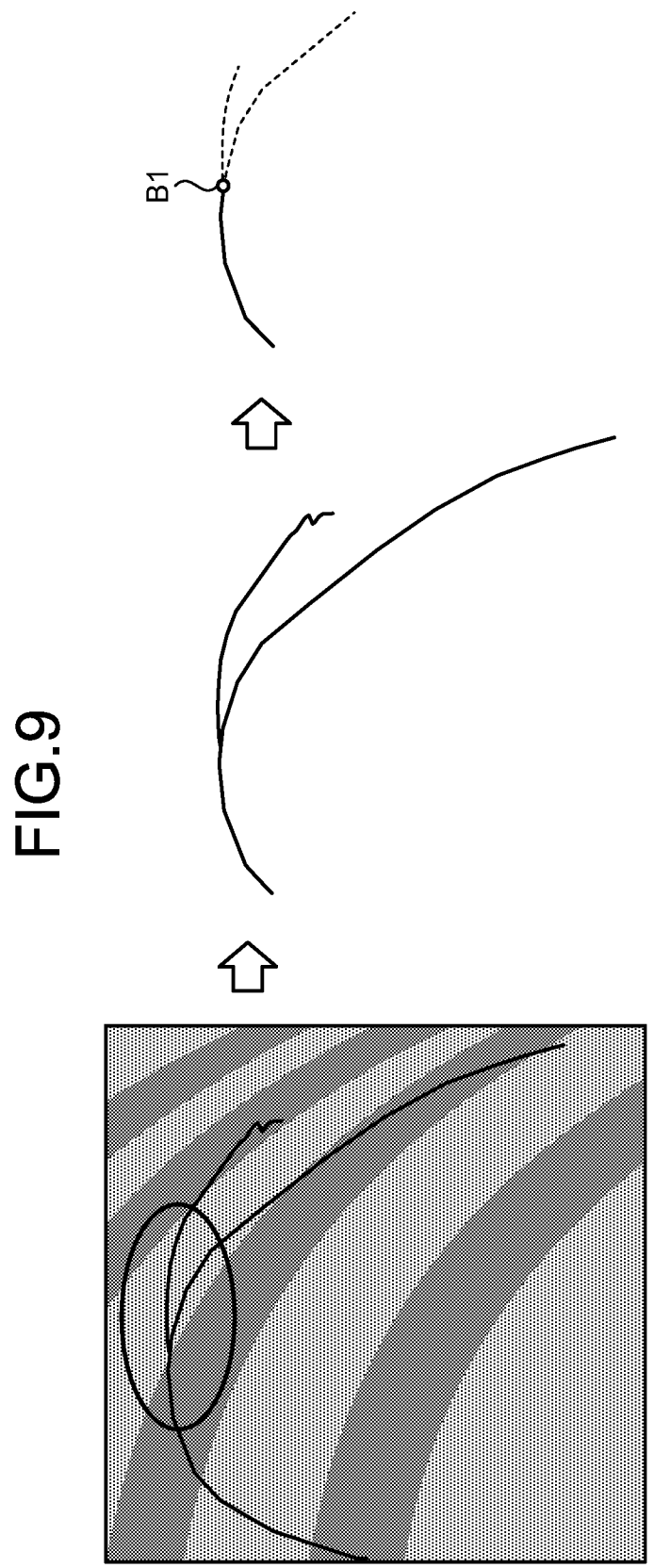
FIG. 9 is a diagram illustrating an example of a device according to the second embodiment.

In the embodiment described above, the portion having a large curvature of the device is described as an example of the characteristic portion. However, the embodiment is not limited thereto. For example, as illustrated in FIG. 9, the processing function 34c may perform the processing of suppressing movement of the characteristic portion assuming that a branch part B1 in a device D2 is the characteristic portion. FIG. 9 is a diagram illustrating an example of the device D2 according to the second embodiment.

For example, first, the processing function 34c extracts an outline of the device D2. Next, the processing function 34c specifies the branch part B1 in the outline of the device D2, and creates an outline model for a portion closer to hands of the user than the branch part B1 (a portion indicated by a solid line in FIG. 9). The processing function 34c then suppresses movement of the branch part B1 by obtaining corresponding points on the outline model among the X-ray images. In obtaining the corresponding points, the processing function 34c may provide a constraint condition so that branch parts B1 in the respective images are associated with each other.

In the embodiment described above, the processing of suppressing movement of the characteristic portion is described to be processing of causing characteristic portions to match each other between the X-ray images as illustrated in FIG. 5, for example. That is, in the embodiment described above, the processing of fixing the characteristic portion is described as the processing of suppressing movement of the characteristic portion. However, the embodiment is not limited thereto. For example, the processing function 34c may perform, as the processing of suppressing movement of the characteristic portion, processing of reducing a difference in the position or orientation of the characteristic portion between the images. That is, the processing of suppressing movement of the characteristic portion may be processing of fixing the characteristic portion, or may be processing of merely reducing movement of the characteristic portion.

In the embodiment described above, the X-ray images in which movement of the characteristic portion is suppressed are assumed to be displayed on the display 32. However, the embodiment is not limited thereto. For example, the output function 34d may transmit the X-ray images in which movement of the characteristic portion is suppressed to another device such as the X-ray diagnostic apparatus 10. In this case, the X-ray image is displayed by the device that has received the image, so that the X-ray images in which movement of the characteristic portion is suppressed can be provided to the user.

Figure 10:
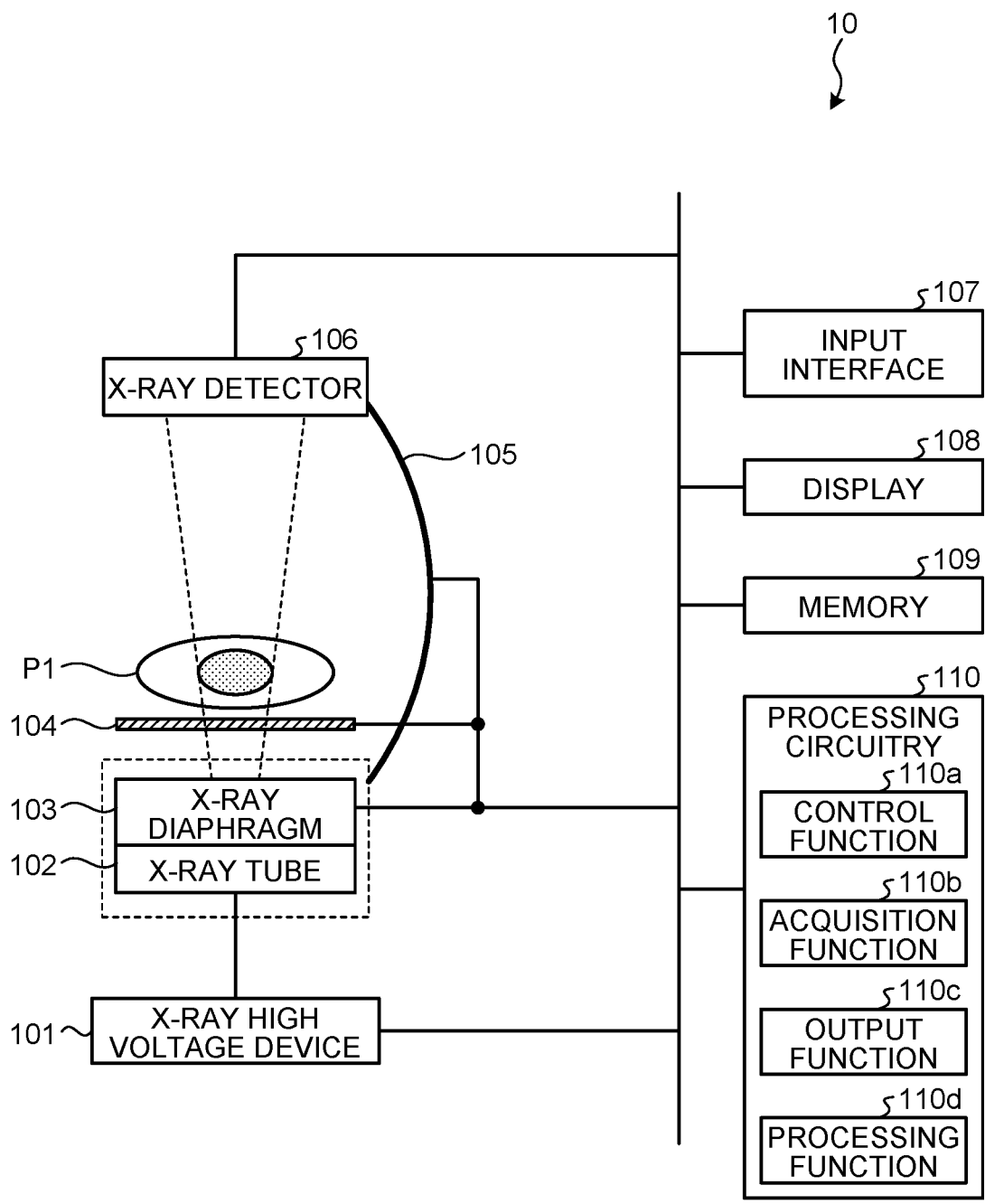
FIG. 10 is a block diagram illustrating an example of a configuration of an X-ray diagnostic apparatus according to the second embodiment.

In the embodiment described above, it is assumed that the medical image processing apparatus 30 performs the processing of suppressing movement of the characteristic portion. However, the embodiment is not limited thereto. For example, the processing circuitry 110 of the X-ray diagnostic apparatus 10 may execute a function corresponding to the processing function 34c described above. This point is described below with reference to FIG. 10. FIG. 10 is a block diagram illustrating an example of a configuration of the X-ray diagnostic apparatus 10 according to the second embodiment. As illustrated in FIG. 10, the processing circuitry 110 executes the control function 110a, the acquisition function 110b, the output function 110c, and the processing function 110d. The processing function 110d is an example of a processing unit.

For example, the acquisition function 110b emits X-rays to the subject P1 in a state in which the device D1 is inserted into his/her body, and detects X-rays transmitted through the subject P1 to acquire the X-ray images. The processing function 110d suppresses movement of the characteristic portion characterized in the shape that is positioned distant from the distal end of the device D1 among the acquired X-ray images. For example, assuming that the X-ray image I131 is the reference frame, the processing function 110d performs matching processing between the X-ray image I131 and the X-ray image I13t that is acquired after the X-ray image I131 to calculate the rotation/translation matrix W. The processing function 110d applies the calculated rotation/translation matrix W to the X-ray image I13t to suppress movement of the characteristic portion between the X-ray image I131 and the X-ray image I13t. The output function 110c causes the display 108 to display the X-ray images in which movement of the characteristic portion is suppressed by the processing function 110d.

In the first and the second embodiments described above, as illustrated in FIG. 4 for example, described is a case of performing the processing of suppressing movement of the characteristic portion characterized in the shape that is positioned distant from the distal end of the device. However, there may be a case in which a portion that is positioned distant from the distal end of the device does not have a characteristic. For example, in a case in which the blood vessel into which the device is inserted has a shape close to a linear shape, the device also has a linear shape, so that there may be a case in which a portion having a large curvature cannot be specified.

Thus, in a third embodiment, visibility of the X-ray image is improved by performing the processing of suppressing movement of the characteristic portion included in the blood vessel image in a corresponding time phase in place of the processing of suppressing movement of the characteristic portion of the device. For example, in a case in which a condition related to a positional relation between the distal end and the characteristic portion is satisfied, the processing circuitry 34 specifies the blood vessel image of a corresponding time phase among blood vessel images of a plurality of time phases for each of the X-ray images. The processing circuitry 34 specifies the processing of suppressing movement of the characteristic portion included in the blood vessel image of the corresponding time phase. The processing circuitry 34 then performs, for the X-ray image, the processing of suppressing movement of the characteristic portion included in the blood vessel image of the corresponding time phase in place of the processing of suppressing movement of the characteristic portion of the device.

In the third embodiment, the medical image processing system 1 illustrated in FIG. 1 is described as an example. For example, the X-ray diagnostic apparatus 10 acquires the blood vessel images from the subject P1 before starting intravascular treatment for the subject P1, and transmits the acquired blood vessel images to the medical image processing apparatus 30. For example, the X-ray diagnostic apparatus 10 acquires two-dimensional X-ray images from the subject P1 over time while intravascular treatment is performed on the subject P1, and successively transmits the acquired X-ray images to the medical image processing apparatus 30.

The medical image processing apparatus 30 acquires the blood vessel images and the X-ray images acquired by the X-ray diagnostic apparatus 10, and performs various kinds of processing using the blood vessel images and the X-ray images. For example, the medical image processing apparatus 30 performs first processing on the blood vessel image, and performs second processing on the X-ray image based on a result of the first processing. The medical image processing apparatus 30 also displays the X-ray image subjected to the second processing.

The processing circuitry 34 reads out a computer program corresponding to the acquisition function 34b from the memory 33 to be executed, for example, and acquires the blood vessel image and the X-ray image of the subject P1. For example, the processing circuitry 34 performs the first processing on the blood vessel image by reading out a computer program corresponding to the processing function 34c from the memory 33 to be executed, and performs the second processing on the X-ray image based on a result of the first processing. For example, the processing circuitry 34 reads out a computer program corresponding to the output function 34d from the memory 33 to be executed, and outputs the X-ray image subjected to the processing performed by the processing function 34c.

For example, the acquisition function 110h acquires the X-ray images over time while intravascular treatment is performed on the subject P1. For example, while the PCI is performed, the acquisition function 110b acquires the X-ray images including a coronary artery in the imaging range over time. The imaging range may be set by the user such as a doctor who performs intravascular treatment, or may be automatically set by the acquisition function 110b based on patient information and the like.

Specifically, the acquisition function 110b controls the irradiation range of the X-rays emitted to the subject P1 by controlling an operation of the X-ray diaphragm 103, and adjusting the opening of the diaphragm blades included in the collimator. The acquisition function 110b controls dose distribution of the X-rays by controlling the operation of the X-ray diaphragm 103, and adjusting the position of the filter. The acquisition function 110b also rotates or moves the C-arm 105 by controlling the operation of the C-arm 105. For example, the acquisition function 110b also moves or inclines the tabletop 104 by controlling the operation of the table. That is, the acquisition function 110b controls the imaging range and the imaging angle of the X-ray image to be acquired by controlling the operation of the mechanical system such as the X-ray diaphragm 103, the C-arm 105, and the tabletop 104.

The acquisition function 110b also controls ON/OFF or the dose of the X-rays emitted to the subject P1 by controlling the X-ray high voltage device 101, and adjusting the voltage supplied to the X-ray tube 102. The acquisition function 110b also generates the X-ray image based on the detection signal received from the X-ray detector 106. In this case, the acquisition function 110b may perform various kinds of image processing on the generated X-ray image. For example, the acquisition function 110b can perform noise reduction processing using an image processing filter, or scattered ray correction on the generated X-ray image.

The output function 110c successively transmits the acquired X-ray images to the medical image processing apparatus 30.

The acquisition function 110b acquires the blood vessel images from the subject P1 before starting intravascular treatment for the subject P1. At this point, the acquisition function 110b acquires the blood vessel images in accordance with the imaging range of the X-ray images that are acquired during the treatment. For example, in a case in which the PCI is performed, the X-ray images including the coronary artery in the imaging range are expected to be acquired, so that the acquisition function 110b acquires the blood vessel images including the coronary artery in the imaging range.

Specifically, the acquisition function 110b acquires the X-ray images by imaging the subject P1 in a state in which the contrast medium is injected into his/her blood vessel. The X-ray image that is acquired in a state in which the contrast medium is injected into the blood vessel is also referred to as a contrast image. The type of the contrast medium is not limited. The contrast medium may be a positive contrast medium containing iodine, barium sulfate, and the like as principal components, or may be a gas contrast medium such as carbon dioxide. The contrast medium may be manually injected by the user such as a doctor, or may be automatically injected by an injector disposed on the X-ray diagnostic apparatus 10.

For example, the acquisition function 110b acquires a plurality of the contrast images by repeatedly emitting X-rays after the contrast medium is injected into the blood vessel of the subject P1. The acquisition function 110b also acquires a plurality of the mask images by repeatedly emitting X-rays before the contrast medium is injected into the blood vessel of the subject P1. The acquisition function 110b then generates a plurality of the blood vessel images by performing difference processing between the mask images and the contrast images. Alternatively, the acquisition function 110b may extract pixels indicating contrast of the blood vessel in the contrast image to generate the blood vessel image by performing threshold processing on a pixel value of the contrast image, or performing semantic segmentation processing on the contrast image without acquiring the mask images. The output function 110c transmits the acquired blood vessel images to the medical image processing apparatus 30.

Figure 11B:
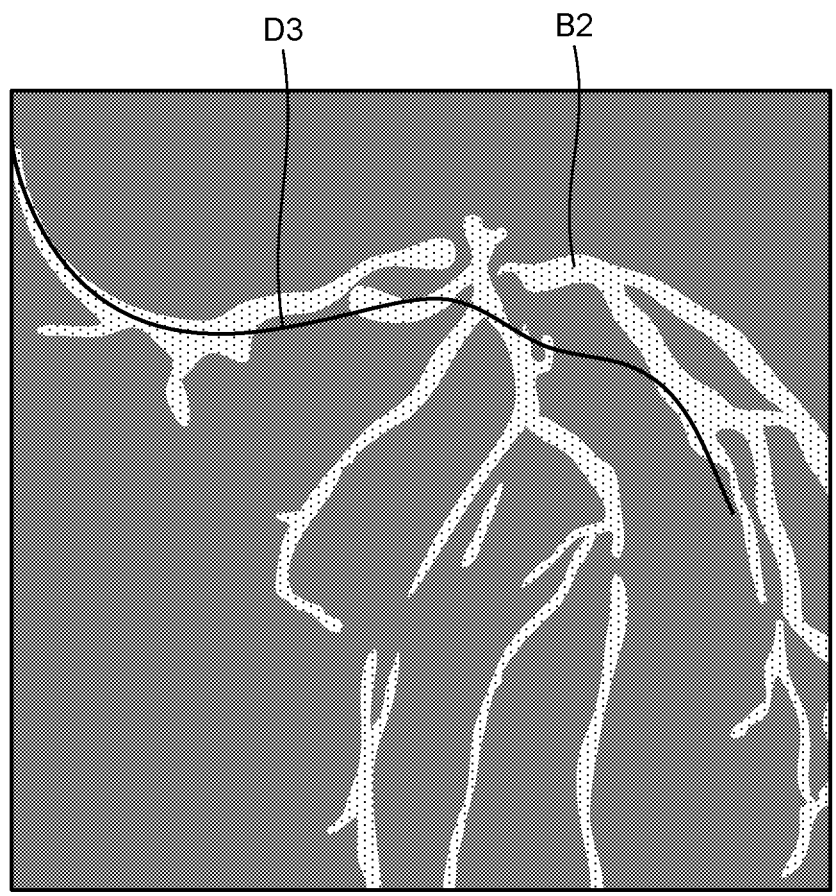
FIG. 11B is a diagram illustrating a display example according to the third embodiment.

The following describes an example of display of the X-ray image by the medical image processing apparatus 30 with reference to FIG. 11A and FIG. 11B. FIG. 11A and FIG. 11B are diagrams illustrating display examples according to the third embodiment. Regarding FIG. 11A and FIG. 11B, described is a case of displaying the X-ray images acquired for coronary arteries of the subject P1. Additionally, regarding FIG. 11A and FIG. 11B, described is a case of synthesizing the X-ray image with the blood vessel image to be displayed.

First, the blood vessel images are acquired before intravascular treatment is started. For example, the acquisition function 110b images the subject P1 in a state in which the contrast medium is injected into his/her blood vessel to acquire X-ray images I211 to I21n illustrated in FIG. 11A. That is, each of the X-ray images I211 to I21n illustrated in FIG. 11A is the contrast image. The acquisition function 110b extracts the blood vessel from the X-ray images I211 to I21n to acquire the blood vessel images I221 to I22n illustrated in FIG. 11A. For example, the acquisition function 110b extracts pixels corresponding to the blood vessel to generate the blood vessel images I221 to I22n by performing threshold processing on pixel values of the X-ray images I211 to I21n. For example, the acquisition function 110b acquires the mask images by imaging the subject P1 before the contrast medium is injected into his/her blood vessel, and performs difference processing between the mask images and the X-ray images I211 to I21n to generate the blood vessel images I221 to I22n.

Next, the acquisition function 34b acquires the blood vessel images I221 to I22n. For example, the output function 110c transmits the blood vessel images I221 to I22n to the image storage device via the network NW. In this case, the acquisition function 34b can acquire the blood vessel images I221 to I22n from the image storage device via the network NW. Examples of such an image storage device include a server of a Picture Archiving Communication System (PACS), for example. Alternatively, the acquisition function 34b may directly acquire the blood vessel images I221 to I22n from the X-ray diagnostic apparatus 10 without using another device.

After the intravascular treatment is started, the acquisition function 110b images the subject P1 in a state in which the device is inserted into his/her blood vessel to acquire the X-ray image I231 illustrated in FIG. 11A. The acquisition function 34b acquires the X-ray image I231. For example, the output function 110c transmits the X-ray image I231 to the image storage device via the network NW. In this case, the acquisition function 34b can acquire the X-ray image I231 from the image storage device via the network NW. Alternatively, the acquisition function 34b may directly acquire the X-ray image I231 from the X-ray diagnostic apparatus 10 without using another device.

The device inserted into the body of the subject P1 typically has a wire shape. Examples of such a wire-shaped device include a catheter and a guide wire used for intravascular treatment. For example, in the PCI, the user such as a doctor operates a guide wire inserted into the body of the subject P1 to move to a lesion. In this case, the lesion is, for example, a constriction of the blood vessel such as Chronic Total Occlusion (CTO). In such a case, the acquisition function 110b acquires the X-ray image I231 so that the imaging range of the X-ray image I231 includes a distal end of the guide wire. The acquisition function 110b can appropriately adjust the imaging range to follow a distal end position of the guide wire when the distal end position of the guide wire moves.

Next, the output function 34d synthesizes the blood vessel image with the X-ray image I231. In this case, the blood vessel images I221 to I22n and the X-ray image I231 are acquired for the coronary arteries of the subject P1, and includes movement caused by heartbeat. The output function 34d then selects one of the blood vessel images I221 to I22n including a phase of heartbeat corresponding to that of the X-ray image I231, and synthesizes the selected image with the X-ray image I231.

For example, the output function 34d can select the blood vessel image of a phase corresponding to the X-ray image I231 based on the phase information. In this case, the phase information is information indicating an aspect of a cardiac cycle in which the image is acquired, for example. For example, the acquisition function 110b acquires the X-ray images I211 to I21n while measuring heartbeat of the subject P1, and attaches the phase information to each of the X-ray images I211 to I21n. The pieces of phase information are inherited by the blood vessel images I221 to I22n that are generated based on the X-ray images I211 to I21n. The acquisition function 110b acquires the X-ray image I231 while measuring heartbeat of the subject P1, and attaches the phase information to the X-ray image I231. The output function 34d then compares the phase information attached to each of the blood vessel images I221 to I22n with the phase information attached to the X-ray image I231, and selects the blood vessel image of a phase corresponding to the X-ray image I231 from among the blood vessel images I221 to I22n. The output function 34d then generates a synthesized image I241 by synthesizing the selected blood vessel image with the X-ray image I231, and causes the display 32 to display the synthesized image I241.

In the synthesized image I241, as illustrated in FIG. 11B for example, a blood vessel B2 in the blood vessel image and a device D3 in the X-ray image I231 are superimposed to be displayed. Due to this, the user who performs intravascular treatment can operate the device D3 while grasping a positional relation between the device D3 and the blood vessel B2.

Similarly to the X-ray image I231, the acquisition function 110b acquires the X-ray images over time. The output function 34d selects a blood vessel image of a corresponding phase from among the blood vessel images I221 to I22n for each of the X-ray images, and generates a synthesized image. Every time the output function 34d generates the synthesized image, the output function 34d causes the display 32 to successively display the newly generated synthesized image. That is, the output function 34d displays the synthesized image in real time. Due to this, the user who performs intravascular treatment can move the device D3 to a lesion such as CTO while grasping a current position of the device D3 with respect to the blood vessel B2.

In a plurality of the synthesized images that are successively displayed, the device D3 and the blood vessel B2 dynamically move in accordance with heartbeat. It may be a burden on the user to follow the device D3 and the blood vessel B2 with eyes for observation, the device D3 and the blood vessel B2 the positions of which change for each frame.

In a case of displaying the X-ray image that is acquired for a moving portion, there is known a technique of displaying the X-ray image while suppressing the movement. For example, in a case in which a marker is added to the device D3, a marker portion of the device D3 can be fixedly displayed by detecting markers from the respective X-ray images to be aligned with each other. The marker is, for example, a metal piece having a predetermined shape and size.

However, in a case of performing such fixed display, visibility of the vicinity of the marker of the device D3 is improved, but visibility of the blood vessel B2 is not necessarily improved. For example, the position of the blood vessel B2 is entirely moved due to heartbeat, and the blood vessel B2 is also deformed. Thus, even when the marker of the device D3 is fixed, the blood vessel B2 is not fixed in many cases.

The user may pay attention to the device D3, or may pay attention to the blood vessel B2 in some cases. For example, the user may observe the synthesized image while paying attention to the blood vessel region to which the device D3 is expected to move, and operate the device D3 in some cases. However, in a case of performing fixed display by detecting the marker of the device D3, a fixing place cannot be changed from the marker. For example, there may be a case in which the blood vessel region to which the device D3 is expected to move is moved, and visibility becomes insufficient for operating the device D3.

The processing circuitry 34 of the medical image processing apparatus 30 then enables suppression of movement at an optional position on the image by performing the first processing and the second processing that are described below in detail, and improves visibility. The following describes processing performed by the processing circuitry 34 with reference to FIG. 12A, FIG. 12B, and FIG. 12C. FIG. 12A, FIG. 12B, and FIG. 12C are diagrams for explaining the first processing and the second processing according to the third embodiment.

First, the processing function 34c selects a blood vessel region as a target of processing of suppressing movement in the blood vessel image. For example, the processing function 34c selects the blood vessel region based on an input operation from the user.

For example, the output function 34d causes the display 32 to display one or a plurality of blood vessel images among the blood vessel images I221 to I22n. By way of example, the output function 34d causes the display 32 to display the blood vessel image I221. The user disposes a rectangular ROI on the blood vessel image I221 corresponding to the blood vessel region where the device D3 is expected to reach. For example, the user disposes the ROI on the blood vessel image I221 corresponding to the blood vessel region as a target reached by the device D3. By way of example, the user disposes the ROI on the blood vessel region as a route for the blood vessel region as a target to be reached. Alternatively, the user may dispose the ROI on the blood vessel region itself as a target to be reached. Due to this, the processing function 34c can select the blood vessel region in the ROI as the blood vessel region for suppressing movement. FIG. 12A illustrates the rectangular ROI, but the shape and the size of the ROI can be optionally changed.

Next, the processing function 34c specifies the first processing of suppressing movement of the selected blood vessel region among the blood vessel images. Regarding FIG. 12A, described is a case of specifying, as the first processing, rotation/translation processing for moving and rotating the blood vessel image so that the position and orientation of the blood vessel region become substantially the same among the blood vessel images. For example, first, the processing function 34c acquires a blood vessel pattern VP of the blood vessel region selected in the blood vessel image I221. Next, the processing function 34c searches for a pattern VP' close to the blood vessel pattern VP in another blood vessel image such as a blood vessel image I222 and a blood vessel image I223.

By way of example, the processing function 34c manages blood vessel patterns included in the respective blood vessel images such as the blood vessel image I222 and the blood vessel image I223 as a tree structure. The blood vessel typically includes branch parts, and the number of the branch parts gradually increases toward an upstream side or a downstream side of a blood flow. Thus, the processing function 34c can provide a node for each of the branch parts, and manage a shape of each branch part as a tree structure. The processing function 34c can search for the pattern VP' at high speed by comparing the shape of each branch part with the blood vessel pattern VP sequentially from a root node toward a leaf node.

Next, the processing function 34c calculates the rotation/translation matrix W based on the position and orientation of the blood vessel pattern VP in the blood vessel image I221, and the position and orientation of the pattern VP' in another blood vessel image. For example, the processing function 34c calculates a rotation/translation matrix W1 based on the blood vessel pattern VP in the blood vessel image I221 and the pattern VP' in the blood vessel image I222. The processing function 34c also calculates a rotation/translation matrix W2 based on the blood vessel pattern VP' in the blood vessel image I222 and the pattern VP' in the blood vessel image I223. That is, the processing function 34c specifies the rotation/translation processing as the first processing by calculating the rotation/translation matrix W1 and the rotation/translation matrix W2.

The processing function 34c then applies the calculated rotation/translation matrix W to each blood vessel image to perform the first processing of suppressing movement of the selected blood vessel region. For example, as illustrated in FIG. 12A, the processing function 34c applies the rotation/translation matrix W1 to the blood vessel image I222 to align the blood vessel image I222 with the blood vessel image I221. The processing function 34c also applies the rotation/translation matrix W1 and the rotation/translation matrix W2 to the blood vessel image I223 to align the blood vessel image I223 with the blood vessel image I221. Due to this, as illustrated in a lower row of FIG. 12A, selected blood vessel regions are aligned with each other among the blood vessel images. That is, in the case illustrated in FIG. 12A, the processing function 34c performs, as the first processing, rotation/translation processing of moving and rotating each of the blood vessel images so that the position and orientation of the blood vessel region in the blood vessel image I221 as the reference frame substantially match those of the blood vessel region in the blood vessel image of a frame different from the reference frame.

Next, the processing function 34c performs the second processing based on a result of the first processing illustrated in FIG. 12A. Specifically, the processing function 34c applies the first processing specified in FIG. 12A to the X-ray images to perform the second processing of suppressing movement among the X-ray images. For example, the processing function 34c aligns the X-ray images with each other as illustrated in FIG. 12B by performing the second processing.

In the description about FIG. 12B, it is assumed that phases of the X-ray image I231 and the blood vessel image I221 correspond to each other, phases of the X-ray image I232 and the blood vessel image I222 correspond to each other, and phases of the X-ray image I233 and the blood vessel image I223 correspond to each other. In this case, for example, the processing function 34c applies the rotation/translation matrix W1 to the X-ray image I232 to align the X-ray image I232 with the X-ray image I231. The processing function 34c also applies the rotation/translation matrix W1 and the rotation/translation matrix W2 to the X-ray image I233 to align the X-ray image I233 with the X-ray image I231. Due to this, similarly to the blood vessel images, the X-ray images are aligned with each other.

That is, the processing function 34c performs the rotation/translation processing, which has been performed on the blood vessel image, on the X-ray image of a corresponding phase as it is as the second processing of suppressing movement among the X-ray images. Due to this, even when the blood vessel does not appear on the X-ray image, regions corresponding to the blood vessel pattern VP are aligned with each other on the X-ray images.

As illustrated in FIG. 12C, the output function 34d then generates a synthesized image of the blood vessel image after the alignment and the X-ray image after the alignment, and causes the display 32 to successively display the synthesized image. For example, the output function 34d generates the synthesized image I241 of the blood vessel image I221 after the alignment and the X-ray image I231 after the alignment, and causes the display 32 to display the synthesized image I241. The output function 34d also generates a synthesized image I242 of the blood vessel image I222 after the alignment and the X-ray image I232 after the alignment, and causes the display 32 to display the synthesized image I242. The output function 34d also generates a synthesized image I243 of the blood vessel image I223 after the alignment and the X-ray image I233 after the alignment, and causes the display 32 to display the synthesized image I243. That is, the output function 34d outputs the synthesized image of the blood vessel image in which movement is suppressed by the first processing, and the X-ray image in which movement is suppressed by the second processing.

Figure 13:
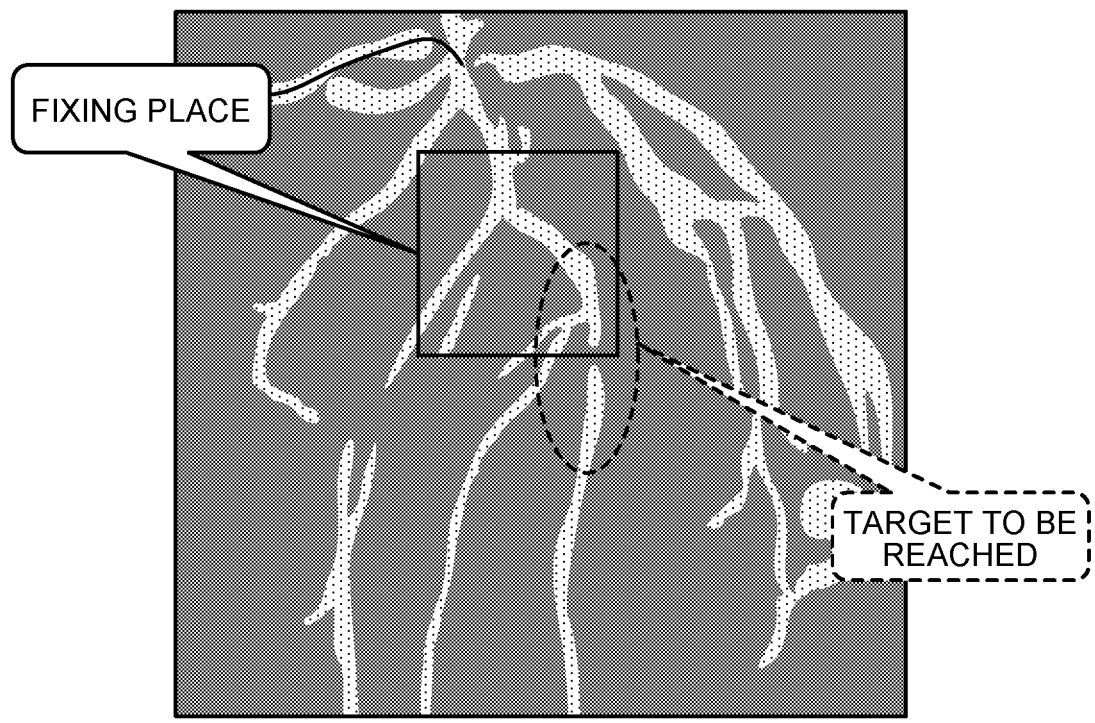
FIG. 13 is a diagram for explaining a fixing place according to the third embodiment.

As illustrated in FIG. 12A, FIG. 12B, and FIG. 12C, the processing function 34c can suppress movement of an optionally selected blood vessel region by performing the first processing and the second processing. For example, in the case illustrated in FIG. 13, the processing function 34c selects the blood vessel region indicated by a rectangle as a fixing place, and suppresses movement in the rectangular region. Due to this, movement of the device D3 in the rectangular region is suppressed in the X-ray image. In the blood vessel image, movement of the blood vessel B2 in the rectangular region is suppressed. In a state in which movement in the rectangular region is suppressed, the device D3 and the blood vessel B2 are synthesized to be displayed. Thus, the user can obtain high visibility in operating the device D3 in the rectangular region, and can easily perform operation of moving the device D3 to a target to be reached, for example. FIG. 13 is a diagram for explaining the fixing place according to the third embodiment.

The blood vessel image I221, the blood vessel image I222, and the blood vessel image I223 illustrated in FIG. 12A may be a series of blood vessel images that are acquired in one time of photographing, or may be a combination of blood vessel images that are acquired in different times of photographing. That is, the processing function 34c may perform the first processing and the second processing described above by using the blood vessel image corresponding to one cut, or may further use a blood vessel image of a different cut, if present, in which the imaging range and the phase on the cardiac cycle substantially match those of the X-ray image.

By way of example, there may be a case in which the blood vessel image of a corresponding phase cannot be specified for part of the X-ray image like a case in which the blood vessel images are acquired at a frame rate of 10 f/s (frame/second), and the X-ray images are acquired at a frame rate of 20 f/s. In a case in which the blood vessel images have been acquired for the same portion at the frame rate of 10 f/s in the past, and phases on the cardiac cycle are shifted from each other by 0.05 s, the processing function 34c can combine these blood vessel images corresponding to two cuts with each other to specify the blood vessel image the phase of which corresponds to each X-ray image. Due to this, even in a case in which the frame rate is different between the blood vessel image and the X-ray image, or the phases on the cardiac cycle are shifted from each other, the processing function 34c can prevent the frame rate from being lowered.

Figure 14:
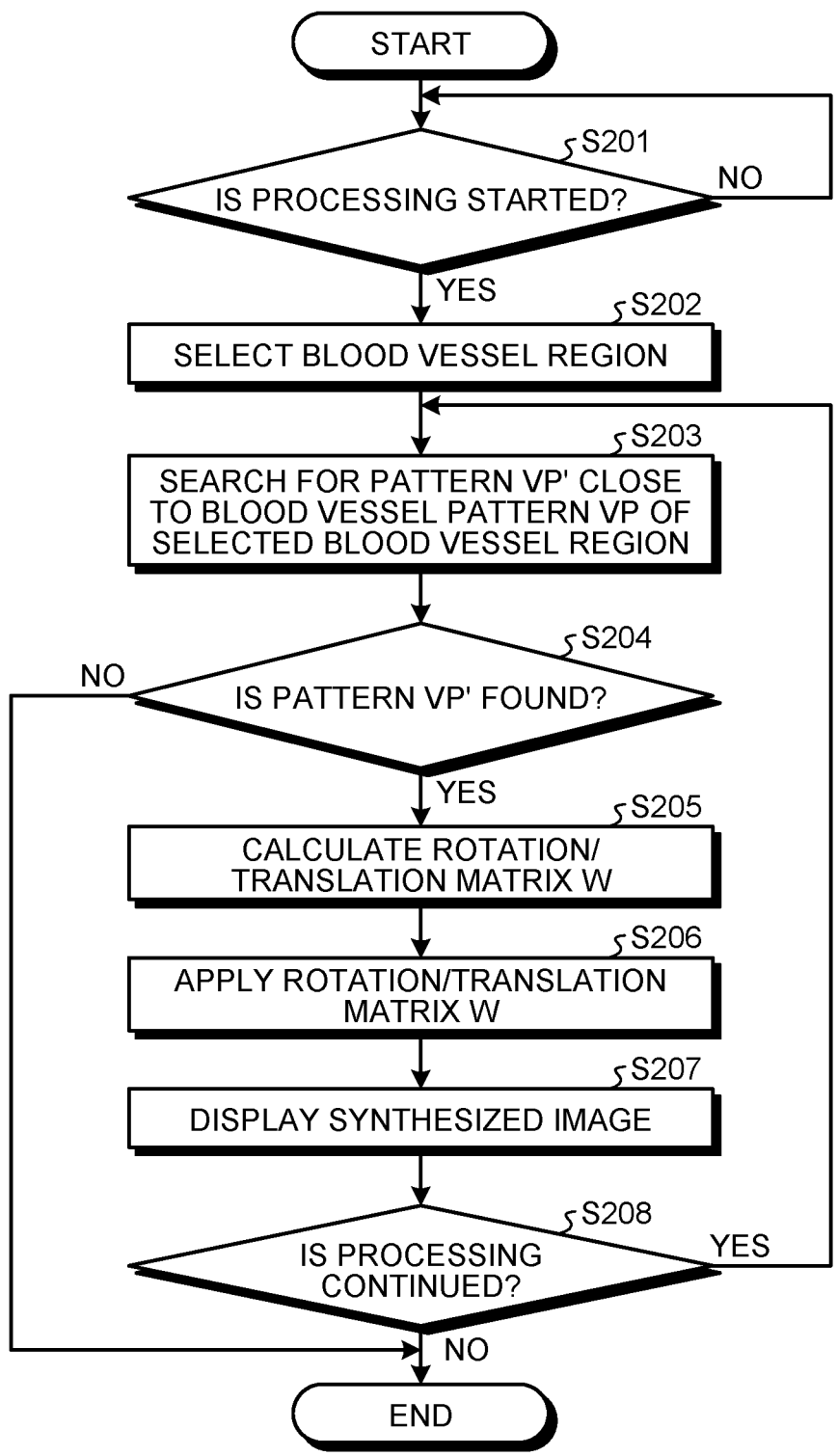
FIG. 14 is a flowchart for explaining a series of procedures of processing performed by the medical image processing apparatus according to the third embodiment.

Next, the following describes an example of a processing procedure performed by the medical image processing apparatus 30 with reference to FIG. 14. FIG. 14 is a flowchart for explaining a series of procedures of processing performed by the medical image processing apparatus 30 according to the third embodiment. Step S201, Step S202, Step S203, Step S204, Step S205, Step S206, and Step S208 are steps corresponding to the processing function 34c. Step S207 is a step corresponding to the output function 34d.

First, the processing circuitry 34 determines whether to start processing of suppressing movement of the X-ray image (Step S201). For example, in a case of controlling the imaging range to follow a distal end position of the device D3, the processing of suppressing movement of the X-ray image is not required in some cases depending on the position of the device D3. For example, in the PCI, the device D3 is inserted from a femoral artery of the subject P1, and moves in the blood vessel toward the heart. In this case, the processing of suppressing movement of the X-ray image is not required when the device D3 is positioned at a leg of the subject P1, and is required when the device D3 approaches the heart and is influenced by heartbeat. Thus, the processing circuitry 34 can determine to start the processing of suppressing movement of the X-ray image when the device D3 reaches the vicinity of the heart.

Determination at Step S201 may be performed by receiving an input operation from the user such as a doctor, or may be automatically performed by the processing circuitry 34 by analyzing the position of the device D3. If the processing is not started (No at Step S201), the processing circuitry 34 is caused to be in a standby state. If the processing is started (Yes at Step S201), the processing circuitry 34 advances the process to Step S202.

Next, the processing circuitry 34 selects the blood vessel region (Step S202). For example, the processing circuitry 34 selects the blood vessel region by causing the display 32 to display the blood vessel image I221, and receiving the input operation from the user. Next, the processing circuitry 34 searches for the pattern VP' close to the blood vessel pattern VP of the selected blood vessel region in each of the blood vessel images other than the blood vessel image I221 (Step S203). If the pattern VP' is not found (No at Step S204), the processing circuitry 34 ends the processing. On the other hand, if the pattern VP' is found (Yes at Step S204), the processing circuitry 34 calculates the rotation/translation matrix W based on the position and orientation of the blood vessel pattern VP in the blood vessel image I221, and the position and orientation of the pattern VP' in the other blood vessel image (Step S205).

Next, the processing circuitry 34 applies the rotation/translation matrix W to each of the images (Step S206). Specifically, the processing circuitry 34 suppresses movement of the blood vessel region among the blood vessel images by applying the rotation/translation matrix W to the blood vessel images. That is, the processing circuitry 34 performs the first processing of suppressing movement of the blood vessel region among the blood vessel images. The processing circuitry 34 also suppresses movement of a region corresponding to the blood vessel region among the X-ray images by applying the rotation/translation matrix W to the X-ray images. That is, the processing circuitry 34 performs the second processing of suppressing movement among the X-ray images based on a result of the first processing. The processing circuitry 34 then causes the display 32 to display a synthesized image of the blood vessel image in which movement is suppressed by the first processing and the X-ray image in which movement is suppressed by the second processing (Step S207).

Next, the processing circuitry 34 determines whether to continue the processing of suppressing movement of the selected blood vessel region (Step S208). If the processing is continued (Yes at Step S208), the process proceeds to Step S203 again. On the other hand, the processing is not continued (No at Step S208), the processing circuitry 34 ends the processing. For example, in a case in which treatment for CTO is performed, the processing circuitry 34 continues the processing of suppressing movement of the blood vessel region as a route for the CTO to enable the device D3 to easily move until the device D3 reaches the CTO. On the other hand, when the device D3 reaches the CTO, the processing circuitry 34 switches the processing to processing of suppressing movement of the device D3 to enable work and the like for expanding the CTO by using the device D3 to be easily performed. That is, when the device D3 reaches the CTO, the processing circuitry 34 determines not to continue the processing of suppressing movement of the selected blood vessel region at Step S208. For example, when the device D3 reaches the CTO, the processing circuitry 34 specifies the position of the marker added to the device D3 in each of the X-ray images, and starts processing of fixedly displaying the marker.

While the processing of FIG. 14 is performed, a working angle may be changed in some cases when the C-arm 105 is operated by the user, for example. That is, an imaging angle may be changed between the blood vessel image and the X-ray image. In such a case, a result of the first processing performed for the blood vessel image cannot be used for suppressing movement of the X-ray image in some cases.

Thus, the processing circuitry 34 may automatically end the processing of suppressing movement of the X-ray image when the imaging angle is changed. Additionally, the processing circuitry 34 may automatically resume the processing of suppressing movement of the X-ray image when the imaging angle is restored. Alternatively, when the imaging angle is changed, the processing circuitry 34 may acquire the blood vessel image corresponding to the changed imaging angle, and continue the processing of suppressing movement of the X-ray image.

As described above, according to the third embodiment, the acquisition function 34*b* acquires the X-ray images and the blood vessel images that are acquired for a periodically moving portion. The processing function 34*c* selects the blood vessel region in the blood vessel image, and specifies the first processing of suppressing movement of the blood vessel region among the blood vessel images. The processing function 34*c* performs the second processing of suppressing movement among the X-ray images by applying the first processing to the X-ray images. The output function 34*d* outputs the X-ray image in which movement is suppressed by the second processing. Thus, the medical image processing apparatus 30 according to the third embodiment can improve visibility of the X-ray images that are acquired for a moving portion.

For example, regarding the X-ray image acquired for a moving portion, the marker added to the device D3 can be specified and fixedly displayed. However, such fixed display has a small number of options for the fixing place, and the blood vessel region that is not reached by the device D3 cannot be fixedly displayed. On the other hand, the medical image processing apparatus 30 according to the third embodiment can improve a degree of freedom for the fixing place. For example, the medical image processing apparatus 30 can fixedly display the blood vessel region that is not reached by the device D3.

The X-ray image acquired for a moving portion does not necessarily include the device D3. For example, at a stage of planning a treatment, the X-ray images may be acquired without inserting the device D3 into the body of the subject P1 in some cases. Even in a case in which the X-ray image includes the device D3, the marker is not necessarily added to the device D3. That is, the X-ray image does not include a characteristic that can be used for alignment in some cases.

Even in such a case, the medical image processing apparatus 30 can suppress movement of the X-ray image via the blood vessel image.

Fourth Embodiment

The third embodiment has been described above, but various different forms can be employed in addition to the embodiment described above.

For example, the third embodiment describes a case of performing the processing of suppressing movement of the characteristic portion included in the blood vessel image of a corresponding time phase in place of the processing of suppressing movement of the characteristic portion of the device. However, the embodiment is not limited thereto. For example, the processing of suppressing movement of the characteristic portion included in the blood vessel image of a corresponding time phase may be performed irrespective of whether the processing of suppressing movement of the characteristic portion of the device is performed. For example, the processing circuitry 34 may perform the processing of suppressing movement of the characteristic portion included in the blood vessel image of a corresponding time phase without determining whether a condition related to the positional relation between the distal end and the characteristic portion is satisfied.

Alternatively, the processing circuitry 34 may perform the processing of suppressing movement of the characteristic portion of the device in place of the processing of suppressing movement of the characteristic portion included in the blood vessel image of a corresponding time phase. For example, as illustrated in FIG. 11B, at the time of moving the device D3 forward in the blood vessel, the blood vessel in which the device D3 is positioned may gradually become fine in some cases. For example, there may be a case in which the blood vessel region cannot be specified in the blood vessel image such as the blood vessel image I221. In such a case, the processing circuitry 34 can perform the processing of suppressing movement of the characteristic portion of the device in place of the processing of suppressing movement of the characteristic portion included in the blood vessel image of a corresponding time phase. For example, the processing circuitry 34 may determine whether the blood vessel region is specified in the blood vessel image such as the blood vessel image I221, and if it is determined that the blood vessel region cannot be specified, the processing circuitry 34 may perform the processing of suppressing movement of the characteristic portion of the device.

In the embodiment described above, described is a case of selecting the blood vessel region the movement of which is suppressed by causing the display 32 to display the blood vessel image such as the blood vessel image I221, and receiving the input operation from the user who has referred to the blood vessel image. However, the embodiment is not limited thereto.

For example, the processing function 34c may receive the input operation from the user via an image other than the blood vessel image, and select the blood vessel region. By way of example, the output function 34d causes the display 32 to display the blood vessel model acquired from the subject P1. Such a blood vessel model can be acquired by scanning the subject P1 into which the contrast medium has been injected by an X-ray Computed Tomography (CT) device, for example. In this case, for example, the user disposes an ROI on the blood vessel model, or designates any of blood vessels on the blood vessel model depending on the blood vessel region as a target reached by the device D3. The processing function 34c specifies the blood vessel in the ROI disposed on the blood vessel model, or the blood vessel region corresponding to the designated blood vessel in the blood vessel image. In this way, the processing function 34c can select the blood vessel region the movement of which is suppressed based on the input operation received from the user via the blood vessel model.

The processing function 34c may also receive the input operation from the user, and select the blood vessel region without using the image. By way of example, the processing function 34c analyzes the blood vessel image, and adds an anatomic label indicating a name of the blood vessel to each blood vessel region included in the blood vessel image. The processing function 34c then receives designation for the name of the blood vessel from the user to select the blood vessel region the movement of which is suppressed.

By way of example, the output function 34d causes the display 108 to display a list indicating names of the blood vessels included in the blood vessel image. The processing function 34c can receive an operation for selecting any of the names of the blood vessels in the list from the user. For example, the processing function 34c can also receive, from the user, an operation of inputting the name of the blood vessel with characters via a keyboard and the like, or a voice input of the name of the blood vessel.

Alternatively, the processing function 34c may automatically select the blood vessel region. For example, the processing function 34c may select, as the blood vessel region the movement of which is suppressed, a region having a predetermined size and a predetermined shape at the center of the blood vessel image.

For example, the processing function 34c may automatically select the blood vessel region the movement of which is suppressed based on the position of the device D3. For example, in a case in which the user performs an operation of moving the device D3 toward a lesion, the processing function 34c may specify a branch part of the closest blood vessel in a moving direction of the device D3 in the blood vessel image, and select the branch part as the blood vessel region the movement of which is suppressed.

In the embodiment described above, it is assumed that the synthesized image is displayed, the synthesized image of the blood vessel image in which movement is suppressed by the first processing and the X-ray image in which movement is suppressed by the second processing. However, the embodiment is not limited thereto, and the output function 34d may cause the display 32 to display the X-ray image in which movement is suppressed by the second processing without being synthesized with the blood vessel image. That is, the medical image processing apparatus 30 may use the blood vessel image only for suppressing movement of the X-ray image, and does not necessarily display the blood vessel image.

In the embodiment described above, it is assumed that the rotation/translation matrix W is calculated by searching for the pattern VP' in the blood vessel image, and movement of the blood vessel region is suppressed among the blood vessel images. That is, the embodiment described above describes a case of performing the first processing by pattern matching. However, the embodiment is not limited thereto.

For example, the processing function 34c can perform the first processing by performing matching processing between the images without searching for a specific pattern. By way of example, the processing function 34c can perform the first processing by endpoint free Dynamic Programming (DP) matching.

For example, the processing function 34c extracts an outline of the blood vessel region from the blood vessel image I221 illustrated in FIG. 12A. Next, the processing function 34c generates the outline model C1 based on the extracted outline. For example, the processing function 34c generates the outline model C1 by extracting a core line of the blood vessel region as the outline, and generates a plurality of apexes along the core line. Similarly, the processing function 34c generates an outline model C2 based on the blood vessel image I222, and generates an outline model C3 based on the blood vessel image I223.

Next, the processing function 34c obtains the corresponding points between the outline models. For example, the processing function 34c defines a cost corresponding to correspondence between the apexes in the outline model C1 and the apexes in the outline model C2, and obtains the corresponding points by minimizing the cost. In this case, for example, the cost can be defined in accordance with a difference between characteristic amounts of the corresponding apexes. For example, the processing function 34c adds, to each of the apexes in the outline model C1 and the outline model C2, a curvature of the blood vessel at a present position as the characteristic amount. The processing function 34c can obtain the corresponding points so that the apexes having substantially the same characteristic amount have a correspondence relation by defining the cost in accordance with the difference between the characteristic amounts and solving a minimization problem for minimizing the cost.

Additionally, the processing function 34c aligns the blood vessel image I222 with the blood vessel image I221 based on the correspondence relation between the apexes. For example, the processing function 34c calculates the rotation/translation matrix W1 for aligning the blood vessel image I222 with the blood vessel image I221 using singular value decomposition and the like based on the correspondence relation between the apexes. Similarly, the processing function 34c calculates the rotation/translation matrix W2 for aligning the blood vessel image I223 with the blood vessel image I222. The processing function 34c then applies the rotation/translation matrix W1 to the blood vessel image I222 to align the blood vessel image I222 with the blood vessel image I221. The processing function 34c applies the rotation/translation matrix W1 and the rotation/translation matrix W2 to the blood vessel image I223 to align the blood vessel image I223 with the blood vessel image I221.

That is, the processing function 34c can calculate the rotation/translation matrix W1 and the rotation/translation matrix W2 by endpoint free DP matching, and perform the first processing. Similarly to the case illustrated in FIG. 12B, the processing function 34c can align the respective X-ray images with each other using the rotation/translation matrix W1 and the rotation/translation matrix W2. That is, the processing function 34c can perform the second processing of suppressing movement among the X-ray images based on a processing result obtained by endpoint free DP matching.

In the embodiment described above, it is assumed that the first processing is performed on a plurality of the blood vessel images to suppress movement in the blood vessel images. However, the first processing is not necessarily performed on the blood vessel images. That is, the processing function 34c may specify the first processing of suppressing movement of the blood vessel region among the blood vessel images, and apply the first processing to the X-ray images without performing the first processing on the blood vessel images to perform the second processing of suppressing movement among the X-ray images.

In the embodiment described above, the coronary artery is explained as an example of a periodically moving portion. However, the embodiment is not limited thereto, and can be similarly applied to various portions influenced by heartbeat. Similarly, the embodiment can also be applied to various portions influenced by respiration. In this case, the processing function 34c can perform the second processing of suppressing movement among the X-ray images by performing rotation/translation processing, which has been performed on the blood vessel image, on the X-ray image of a corresponding phase based on a phase in a respiration cycle.

In the embodiment described above, in the description about the processing of suppressing movement of the blood vessel region, it is assumed that the blood vessel regions in the respective blood vessel images are caused to match each other as illustrated in FIG. 12A, for example. That is, in the embodiment described above, the processing of fixing the blood vessel region is described as the processing of suppressing movement of the blood vessel region. However, the embodiment is not limited thereto. For example, as the processing of suppressing movement of the blood vessel region, the processing function 34c may perform processing of reducing a difference in the position or orientation of the blood vessel region among the images. That is, the processing of suppressing movement of the blood vessel region may be the processing of fixing the blood vessel region, or may be the processing of merely reducing movement of the blood vessel region. Similarly, the processing of suppressing movement of the X-ray image may be processing of fixing a region corresponding to the blood vessel region selected in the X-ray image, or may be processing of merely reducing movement of the region.

In the embodiment described above, described is the case of specifying the rotation/translation processing as the first processing. That is, in the embodiment described above, described is the case of correcting the position and orientation of the blood vessel region in the processing of suppressing movement of the blood vessel region. However, the embodiment is not limited thereto. The processing function 34c may correct only one of the position and orientation of the blood vessel region.

In a case of correcting the position of the blood vessel region, the processing function 34c specifies, as the first processing, processing of aligning the blood vessel images with each other so that the position of the blood vessel region in the blood vessel image I221 as the reference frame substantially matches the position of the blood vessel region in the blood vessel image of a frame different from the reference frame, for example. For example, the processing function 34c specifies, as the first processing, a translation matrix for translating each blood vessel image. The processing function 34c then performs, as the second processing, alignment processing specified as the first processing on the X-ray image the phase of which corresponds to that of each blood vessel image. Due to this, the processing function 34c can suppress movement among the X-ray images.

In a case of correcting the position of the blood vessel region, for example, the processing function 34c specifies, as the first processing, processing of rotating each blood vessel image so that the orientation of the blood vessel region in the blood vessel image I221 as the reference frame substantially matches the orientation of the blood vessel region in the blood vessel image of a frame different from the reference frame. For example, the processing function 34c specifies, as the first processing, a rotation matrix for rotating each blood vessel image. The processing function 34c then performs, as the second processing, rotation processing specified as the first processing on the X-ray image the phase of which corresponds to that of each blood vessel image. Due to this, the processing function 34c can suppress movement among the X-ray images.

In the embodiment described above, it is assumed that the display 32 is caused to display the X-ray image in which movement is suppressed by the second processing. However, the embodiment is not limited thereto. For example, the output function 34d may transmit the X-ray image in which movement is suppressed to another device such as the X-ray diagnostic apparatus 10. In this case, the X-ray image in which movement is suppressed can be provided to the user by being displayed on the device that has received the image.

In the embodiment described above, it is assumed that the X-ray diagnostic apparatus 10 acquires the blood vessel images from the subject P1. However, the embodiment is not limited thereto. That is, the blood vessel images may be acquired by another X-ray diagnostic apparatus other than the X-ray diagnostic apparatus 10.

In the embodiment described above, it is assumed that the medical image processing apparatus 30 performs the processing of suppressing movement of the X-ray image. However, the embodiment is not limited thereto. For example, a function corresponding to the processing function 34c described above may be executed by the processing circuitry 110 of the X-ray diagnostic apparatus 10. This point is described below with reference to FIG. 10. As illustrated in FIG. 10, the processing circuitry 110 executes the control function 110a, the acquisition function 110b, the output function 110c, and the processing function 110d. The processing function 110d is an example of a processing unit.

For example, the acquisition function 110b acquires the X-ray images for a periodically moving portion of the subject P1. The processing function 110d selects the blood vessel region in the blood vessel image that is acquired for a periodically moving portion of the subject P1. In this case, the blood vessel image may be acquired from the subject P1 by the acquisition function 110b, or may be a blood vessel image that is acquired by another device and acquired therefrom via the network NW. Next, the processing function 110d performs the first processing of suppressing movement of the selected blood vessel region among the blood vessel images. Next, the processing function 110d performs the second processing of suppressing movement among the X-ray images based on a result of the first processing. The output function 110c then outputs the X-ray image in which movement is suppressed by the second processing. For example, the output function 110c causes the display 108 to display the synthesized image of the blood vessel image in which movement is suppressed by the first processing and the X-ray image in which movement is suppressed by the second processing.

The word of "processor" used in the above description means, for example, a circuit such as a CPU, a graphics processing unit (GPU), an application specific integrated circuit (ASIC), and a programmable logic device (for example, a simple programmable logic device (SPLD), a complex programmable logic device (CPLD), and a field programmable gate array (FPGA)). For example, in a case in which the processor is a CPU, the processor implements a function by reading out and executing a computer program stored in a storage circuit. On the other hand, in a case in which the processor is an ASIC, for example, the function is directly incorporated in a circuit of the processor as a logic circuit instead of storing the computer program in the storage circuit. Each of the processors in the embodiments is not necessarily configured as a single circuit. A plurality of independent circuits may be combined to constitute one processor to implement the function. A plurality of constituent elements in the respective drawings may be integrated into one processor to implement the function.

Regarding FIG. 1, it is assumed that the single memory 33 stores the computer programs corresponding to the respective processing functions of the processing circuitry 34. Regarding FIG. 2 and FIG. 7, it is assumed that the single memory 109 stores the computer programs corresponding to the respective processing functions of the processing circuitry 110. However, the embodiment is not limited thereto. For example, a plurality of the memories 33 may be disposed in a distributed manner, and the processing circuitry 34 may be configured to read out a corresponding computer program from each of the memories 33. Similarly, a plurality of the memories 109 may be disposed in a distributed manner, and the processing circuitry 110 may be configured to read out a corresponding computer program from each of the memories 109. Instead of storing the computer program in the memory, the computer program may be directly incorporated in the circuit of the processor. In this case, the processor implements the function by reading out and executing the computer program incorporated into the circuit.

The constituent elements of the devices according to the embodiments described above are merely conceptual, and it is not required that they are physically configured as illustrated necessarily. That is, specific forms of distribution and integration of the devices are not limited to those illustrated in the drawings. All or part thereof may be functionally or physically distributed/integrated in arbitrary units depending on various loads or usage states. Furthermore, all or optional part of the processing functions executed by the respective devices may be implemented by a CPU and a computer program that is analyzed and executed by the CPU, or may be implemented as hardware using wired logic.

The medical image processing method described above in the embodiments can be implemented by executing a computer program prepared in advance by a computer such as a personal computer or a workstation. The computer program can be distributed via a network such as the Internet. Additionally, the computer program can be recorded in a computer-readable non-transitory recording medium such as a hard disk, a flexible disk (FD), a CD-ROM, an MO, and a DVD, and can be executed by being read out from the recording medium by a computer.

According to one of the embodiments described above, visibility of the X-ray image acquired for a moving portion can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
 processing circuitry configured to
  acquire a plurality of X-ray images that include a device having a wire shape and being inserted into a body of a subject, suppress, among the X-ray images, movement of a characteristic portion of the device characterized in a shape and that is positioned distant from a distal end of the device, by performing a matching process of the characteristic portion, wherein the characteristic portion is a portion of the device having a curvature exceeding a threshold, and display, on a display, suppressed images, obtained from the X-ray images, in which the movement of the characteristic portion is suppressed by having performed the matching process of the characteristic portion.

2. The medical image processing apparatus according to claim 1, wherein the processing circuitry is further configured to suppress movement of the characteristic portion by performing the matching processing on the X-ray images.

3. The medical image processing apparatus according to claim 2, wherein the processing circuitry is further configured to suppress the movement of the characteristic portion by performing the matching processing between the X-ray image of a reference frame and the X-ray image of a frame other than the reference frame.

4. The medical image processing apparatus according to claim 3, wherein the processing circuitry is further configured to periodically update the reference frame.

5. The medical image processing apparatus according to claim 2, comprising:
a memory storing a blood vessel image acquired from the subject, wherein the processing circuitry is further configured to
perform correction processing for the blood vessel image based on a result of the matching processing, and
display a synthesized image of the X-ray image in which the movement of the characteristic portion is suppressed and the blood vessel image after the correction processing.

6. The medical image processing apparatus according to claim 2, comprising:
a memory storing a blood vessel image acquired from the subject, wherein the processing circuitry is further configured to
perform correction processing for the blood vessel image based on the characteristic portion, and
display a synthesized image of the X-ray image in which the movement of the characteristic portion is suppressed and the blood vessel image after the correction processing.

7. The medical image processing apparatus according to claim 1, wherein the processing circuitry is further configured to extract the characteristic portion from each of the X-ray images, and perform the matching processing of the characteristic portion on the X-ray images, to suppress the movement of the characteristic portion.

8. The medical image processing apparatus according to claim 1, wherein the processing circuitry is further configured to perform the matching process by adding the curvature, as a characteristic amount, to each of apexes on a curve representing an outline of the device extracted from each of the X-ray images, and obtaining corresponding points between different X-ray images so that the apexes having substantially a same characteristic amount have a correspondence relation.

9. The medical image processing apparatus according to claim 1, wherein the processing circuitry is further configured to perform the matching process by cutting out a portion, as a pattern, corresponding to the characteristic portion in an outline of the device extracted from an image included in the X-ray images, and performing pattern matching on another image included in the X-ray images using the pattern.

10. An X-ray diagnostic apparatus, comprising:
processing circuitry configured to
acquire a plurality of X-ray images including a device having a wire shape and being inserted into a body of a subject,
suppress, among the X-ray images, movement of a characteristic portion of the device characterized in a shape and that is positioned distant from a distal end of the device, by performing a matching process of the characteristic portion, wherein the characteristic portion is a portion of the device having a curvature exceeding a threshold, and
display, on a display, suppressed images, obtained from the X-ray images, in which the movement of the characteristic portion is suppressed by having performed the matching processing of the characteristic portion.

11. The medical image processing apparatus according to claim 1, comprising:
a memory storing blood vessel images of a plurality of time phases that are acquired for the subject, wherein,
when a condition related to a positional relation between the distal end and the characteristic portion is satisfied, the processing circuitry is further configured to
determine a blood vessel image of a corresponding time phase among the blood vessel images of the time phases for each X-ray image of the plurality of X-ray images,
determine processing of suppressing the movement of the characteristic portion included in the blood vessel image of the corresponding time phase, and
perform, for each X-ray image, the processing of suppressing the movement of the characteristic portion included in the blood vessel image of a corresponding time phase in place of the processing of suppressing the movement of the characteristic portion of the device.

12. A medical image processing method, comprising:
acquiring a plurality of X-ray images including a device having a wire shape and being inserted into a body of a subject;
suppressing, among the X-ray images, movement of a characteristic portion of the device characterized in a shape and that is positioned distant from a distal end of the device, by having performed a matching process of the characteristic portion, wherein the characteristic portion is a portion of the device having a curvature exceeding a threshold; and
displaying, on a display, suppressed images, obtained from the X-ray images, in which movement of the characteristic portion is suppressed by having performed the matching processing of the characteristic portion.

13. A medical image processing apparatus, comprising:
processing circuitry configured to
acquire a plurality of blood vessel images acquired for a periodically moving portion, and a plurality of X-ray images acquired for the portion,
select a blood vessel region in the blood vessel images, specify first processing of suppressing movement of the blood vessel region among the blood vessel images, and perform second processing of suppressing movement among the X-ray images by applying the first processing to the X-ray images, and output the X-ray images in which the movement is suppressed by the second processing, the processing circuitry is further configured to specify, as the first processing, a processing of aligning a second blood vessel image so that a position of the blood vessel region in a first blood vessel image of a reference frame substantially matches a position of the blood vessel region in the second blood vessel image of a frame different from the reference frame, and perform, as the second processing, the processing of aligning an X-ray image including a phase in periodic movement corresponding to the second blood vessel image.

14. The medical image processing apparatus according to claim 13, wherein the processing circuitry is further configured to suppress movement in the blood vessel images by performing the first processing on the blood vessel images, and output a synthesized image of the blood vessel image in which the movement is suppressed by the first processing and the X-ray image in which the movement is suppressed by the second processing.

15. An X-ray diagnostic apparatus, comprising:
processing circuitry configured to
acquire a plurality of X-ray images for a periodically moving portion,
select a blood vessel region in a blood vessel image acquired for the portion, specify a first processing of suppressing movement of the blood vessel region among a plurality of the blood vessel images, and perform a second processing of suppressing movement among the X-ray images by applying the first processing to the X-ray images, and
output the X-ray images in which movement is suppressed by the second processing,
the processing circuitry is further configured to specify, as the first processing, a processing of aligning a second blood vessel image so that a position of the blood vessel region in a first blood vessel image of a reference frame substantially matches a position of the blood vessel region in the second blood vessel image of a frame different from the reference frame, and perform, as the second processing, the processing of aligning an X-ray image including a phase in periodic movement corresponding to the second blood vessel image.

16. A medical image processing method, comprising:
acquiring a plurality of blood vessel images acquired for a periodically moving portion, and a plurality of X-ray images acquired for the portion;
selecting a blood vessel region in the blood vessel images, specify a first processing of suppressing movement of the blood vessel region among the blood vessel images, and performing a second processing of suppressing movement among the X-ray images by applying the first processing to the X-ray images; and
outputting the X-ray images in which movement is suppressed by the second processing,
wherein the step of specifying the first processing includes specifying, as the first processing, a processing of aligning a second blood vessel image so that a position of the blood vessel region in a first blood vessel image of a reference frame substantially matches a position of the blood vessel region in the second blood vessel image of a frame different from the reference frame, and the step of performing the second processing includes performing, as the second processing, the processing of aligning the X-ray image including a phase in periodic movement corresponding to the second blood vessel image.

17. A medical image processing apparatus, comprising:
processing circuitry configured to
acquire a plurality of blood vessel images acquired for a periodically moving portion, and a plurality of X-ray images acquired for the portion,
select a blood vessel region in the blood vessel images, specify first processing of suppressing movement of the blood vessel region among the blood vessel images, and perform second processing of suppressing movement among the X-ray images by applying the first processing to the X-ray images, and
output the X-ray images in which the movement is suppressed by the second processing, wherein the processing circuitry is further configured to specify, as the first processing, a processing of rotating a second blood vessel image so that an orientation of the blood vessel region in a first blood vessel image of a reference frame substantially matches an orientation of the blood vessel region in the second blood vessel image of a frame different from the reference frame, and perform, as the second processing, the processing of rotating an X-ray image including a phase in periodic movement corresponding to the second blood vessel image.

18. A medical image processing apparatus, comprising:
processing circuitry configured to
acquire a plurality of blood vessel images acquired for a periodically moving portion, and a plurality of X-ray images acquired for the portion,
select a blood vessel region in the blood vessel images, specify first processing of suppressing movement of the blood vessel region among the blood vessel images, and perform second processing of suppressing movement among the X-ray images by applying the first processing to the X-ray images, and
output the X-ray images in which the movement is suppressed by the second processing, wherein the processing circuitry is further configured to specify, as the first processing, a rotation/translation processing of moving and rotating a second blood vessel image so that a position and an orientation of the blood vessel region in a first blood vessel image of a reference frame substantially matches a position and an orientation of the blood vessel region in the second blood vessel image of a frame different from the reference frame, and perform, as the second processing, the rotation/translation processing on an X-ray image including a phase in periodic movement corresponding to the second blood vessel image.

19. An X-ray diagnostic apparatus, comprising:
processing circuitry configured to
acquire a plurality of X-ray images for a periodically moving portion,
select a blood vessel region in a blood vessel image acquired for the portion, specify a first processing of suppressing movement of the blood vessel region among a plurality of the blood vessel images, and perform a second processing of suppressing movement among the X-ray images by applying the first processing to the X-ray images, and
output the X-ray images in which movement is suppressed by the second processing, wherein the processing circuitry is further configured to specify, as the first processing, a processing of rotating a second blood vessel image so that an orientation of the blood vessel region in a first blood vessel image of a reference frame substantially matches an orientation of the blood vessel region in the second blood vessel image of a frame different from the reference frame, and perform, as the second processing, the processing of rotating an X-ray image including a phase in periodic movement corresponding to the second blood vessel image.

20. An X-ray diagnostic apparatus, comprising:
processing circuitry configured to
    acquire a plurality of X-ray images for a periodically moving portion,
    select a blood vessel region in a blood vessel image acquired for the portion, specify a first processing of suppressing movement of the blood vessel region among a plurality of the blood vessel images, and perform a second processing of suppressing movement among the X-ray images by applying the first processing to the X-ray images, and
    output the X-ray images in which movement is suppressed by the second processing, wherein the processing circuitry is further configured to specify, as the first processing, a rotation/translation processing of moving and rotating a second blood vessel image so that a position and an orientation of the blood vessel region in a first blood vessel image of a reference frame substantially matches a position and an orientation of the blood vessel region in the second blood vessel image of a frame different from the reference frame, and perform, as the second processing, the rotation/translation processing on an X-ray image including a phase in periodic movement corresponding to the second blood vessel image.

21. A medical image processing method, comprising:
acquiring a plurality of blood vessel images acquired for a periodically moving portion, and a plurality of X-ray images acquired for the portion;
selecting a blood vessel region in the blood vessel images, specifying a first processing of suppressing movement of the blood vessel region among the blood vessel images, and performing a second processing of suppressing movement among the X-ray images by applying the first processing to the X-ray images; and
outputting the X-ray images in which movement is suppressed by the second processing,
wherein the step of specifying the first processing includes specifying, as the first processing, a processing of rotating a second blood vessel image so that an orientation of the blood vessel region in a first blood vessel image of a reference frame substantially matches an orientation of the blood vessel region in the second blood vessel image of a frame different from the reference frame, and
the step of performing the second processing includes performing, as the second processing, the processing of rotating an X-ray image including a phase in periodic movement corresponding to the second blood vessel image.

22. A medical image processing method, comprising:
acquiring a plurality of blood vessel images acquired for a periodically moving portion, and a plurality of X-ray images acquired for the portion;
selecting a blood vessel region in the blood vessel images, specifying a first processing of suppressing movement of the blood vessel region among the blood vessel images, and performing a second processing of suppressing movement among the X-ray images by applying the first processing to the X-ray images; and
outputting the X-ray images in which movement is suppressed by the second processing,
wherein the step of specifying the first processing includes specifying, as the first processing, a rotation/translation processing of moving and rotating a second blood vessel image so that a position and an orientation of the blood vessel region in a first blood vessel image of a reference frame substantially matches a position and an orientation of the blood vessel region in the second blood vessel image of a frame different from the reference frame, and
the step of performing the second processing includes performing, as the second processing, the rotation/translation processing on an X-ray image including a phase in periodic movement corresponding to the second blood vessel image.

* * * * *